United States Patent
Hook et al.

(10) Patent No.: US 11,786,498 B2
(45) Date of Patent: Oct. 17, 2023

(54) SACUBITRIL CALCIUM SALTS

(71) Applicant: Novartis AG, Basel (CH)

(72) Inventors: David Hook, Rheinfelden (CH); Bin Hu, Green Brook, NJ (US); Florian Karl Kleinbeck, Zurich (CH); Ulrich Meier, Riehen (CH); Sibylle Mueller, Frenkendorf (CH); Jean-Paul Mutz, Blotzheim (FR); Jan Schlomach, Basel (CH); Paul Allen Sutton, Getzville, NY (US); Liladhar Murlidhar Waykole, Succasunna, NJ (US); Bernhard Wietfeld, Efringen-Kirchen (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/737,985

(22) PCT Filed: Jul. 2, 2015

(86) PCT No.: PCT/US2015/039010
§ 371 (c)(1),
(2) Date: Dec. 19, 2017

(87) PCT Pub. No.: WO2017/003483
PCT Pub. Date: Jan. 5, 2017

(65) Prior Publication Data
US 2018/0296519 A1  Oct. 18, 2018

(51) Int. Cl.
*A61K 31/22* (2006.01)
*A61P 9/10* (2006.01)
(Continued)

(52) U.S. Cl.
CPC ............... *A61K 31/22* (2013.01); *A61P 9/06* (2018.01); *A61P 9/10* (2018.01); *A61P 9/12* (2018.01);
(Continued)

(58) Field of Classification Search
CPC .. A61K 31/22; A61K 31/4178; A61K 31/423; A61K 2300/00; A61P 9/10;
(Continued)

(56) References Cited

U.S. PATENT DOCUMENTS 5,217,896 A   6/1993 Ksander

FOREIGN PATENT DOCUMENTS

| CN | 106065006 A | 4/2015 |
| CN | 106065006 A1 | 11/2016 |

(Continued)

OTHER PUBLICATIONS

"Calcium bis(4-{{2S,4R}-1-(biphenyl-4-yl}-5-ethoxy-4-methyl-5-oxopentan-2-yl}amino}-4-oxobutanoate)", ECHA, Jan. 17, 2012 (Jan. 17, 2012), XP002754412, Retrieved from the Internet: URL:http:f-fecha.europa.eujregistration-dossier/-/registered-dossier/7287 [retrieved on Feb. 17, 2016].
(Continued)

*Primary Examiner* — Savitha M Rao
*Assistant Examiner* — Andrew P Lee
(74) *Attorney, Agent, or Firm* — Timothy P. O'Dea

(57) ABSTRACT

The invention relates to polymorphic forms of the calcium salt of N-(3-carboxyl-1-oxopropyl)-(4S)-(p-phenylphenylmethyl)-4-amino-(2R)-methyl butanoic acid ethyl ester. The calcium salt of N-(3-carboxyl-1-oxopropyl)-(4S)-(p-phenylphenylmethyl)-4-amino-(2R)-methyl butanoic acid ethyl ester is useful in the treatment of various conditions and disorders responsive to the inhibition of neutral endopeptidases.

12 Claims, 10 Drawing Sheets

(51) Int. Cl.
*A61P 9/06* (2006.01)
*A61P 25/02* (2006.01)
*C07C 229/34* (2006.01)
*A61P 9/12* (2006.01)
*A61P 25/06* (2006.01)
*A61K 31/4178* (2006.01)
*A61K 31/423* (2006.01)

(52) U.S. Cl.
CPC ............... *A61P 25/02* (2018.01); *A61P 25/06* (2018.01); *C07C 229/34* (2013.01); *A61K 31/4178* (2013.01); *A61K 31/423* (2013.01); *A61K 2300/00* (2013.01); *C07B 2200/13* (2013.01)

(58) Field of Classification Search
CPC .... A61P 9/06; A61P 25/02; A61P 9/12; A61P 25/06; C07C 229/34; C07B 2200/13
See application file for complete search history.

(56) References Cited

FOREIGN PATENT DOCUMENTS

| | | | |
|---|---|---|---|
| JP | H05-310664 A | 11/1993 | |
| WO | WO 2007/056546 A1 | 5/2007 | |
| WO | WO-2007056546 A1 * | 5/2007 | ........... A61K 31/216 |
| WO | WO2008/031567 A1 | 3/2008 | |
| WO | WO2008/083967 A2 | 7/2008 | |
| WO | WO-2008083967 A2 * | 7/2008 | ........... C07C 227/16 |
| WO | WO2016029828 A1 | 3/2016 | |
| WO | WO2016074651 A1 | 5/2016 | |

OTHER PUBLICATIONS

Caira, "Crystalline Polymorphism of Organic Compounds", Topics in Current Chemistry, vol. 198, pp. 163-208, 1998.
Hirayama, R, "Handbook of Organic Compound Crystal Preparation-Principle and know-how", Maruzen Co., Ltd. (Jul. 25, 2008), Chapter 4, p. 57-84 (Specifically Chapter 4, p. 58, lines 22-28, and p. 78, line 16 to p. 79, line 9).

* cited by examiner

SACUBITRIL CALCIUM SALTS

RELATED APPLICATIONS

This application is a national stage application, filed under 35 U.S.C. § 371, of International Application No. PCT/US2015/039010, filed Jul. 2, 2015, the entire contents of which are incorporated herein by reference in its entirety.

FIELD OF THE INVENTION

The present disclosure generally relates to the calcium salt of N-(3-carboxyl-1-oxopropyl)-(4S)-(p-phenylphenylmethyl)-4-amino-(2R)-methyl butanoic acid ethyl ester (AHU377, also known as sacubitril). The present disclosure particularly relates to polymorphic forms of the calcium salt of AHU377. The present disclosure also generally relates to a pharmaceutical composition comprising the polymorphic forms, methods of using the polymorphic forms in the treatment of various conditions and disorders responsive to the inhibition of neutral endopeptidase (EC 3.4.24.11), and methods for obtaining the polymorphic forms.

BACKGROUND OF THE INVENTION

Polymorphism is the existence of different crystalline forms of a single compound in its solid states. Thus, polymorphs have the same molecular formula but distinct physical properties. Thus, a single compound may have different polymorphic forms where each form has different and distinct physical properties, such as solubility, melting point, and/or X-ray diffraction pattern.

In the art biaryl substituted phosphonic acid derivatives are known which are useful as neutral endopeptidase (NEP) inhibitors, e.g. as inhibitors of the ANF-degrading enzyme in mammals, so as to prolong and potentiate the diuretic, natriuretic and vasodilator properties of ANF in mammals by inhibiting the degradation thereof to less active metabolites. NEP inhibitors are thus particularly useful for the treatment of conditions and disorders responsive to the inhibition of neutral endopeptidase (EC 3.4.24.11), particularly cardiovascular disorders such as hypertension, renal insufficiency including edema and salt retention, pulmonary edema and congestive heart failure.

Several dicarboxylic acid dipeptide neutral endopeptidase (NEP) inhibitors are described in G. M. Kasander et al., *J. Med. Chem.* 1995, 38, 1689-1700, "Dicarboxylic Acid Dipeptide Neutral Endopeptidase (NEP) inhibitors". The said document discloses the sodium salt of N-(3-carboxyl-1-oxopropyl)-(4S)-(p-phenylphenylmethyl)-4-amino-(2R)-methyl butanoic acid ethyl ester. Said compound is actually a prodrug form of the actual NEP inhibitor N-(3-carboxyl-1-oxopropyl)-(4S)-(p-phenylphenylmethyl)-4-amino-(2R)-methyl butanoic acid, but is for ease of reference also referred to as a NEP inhibitor in the following, this term also including any of the modifications of the calcium salt mentioned herein.

U.S. Pat. No. 5,217,996 also discloses N-(3-carboxyl-1-oxopropyl)-(4S)-(p-phenylphenylmethyl)-4-amino-(2R)-methyl butanoic acid ethyl ester and its sodium salt form.

WO 2008/031567 generally disclose the reaction scheme to obtain the calcium salt of N-(3-carboxyl-1-oxopropyl)-(4S)-(p-phenylphenylmethyl)-4-amino-(2R)-methyl butanoic acid ethyl ester; however the process for the preparation of the same is not disclosed in detail.

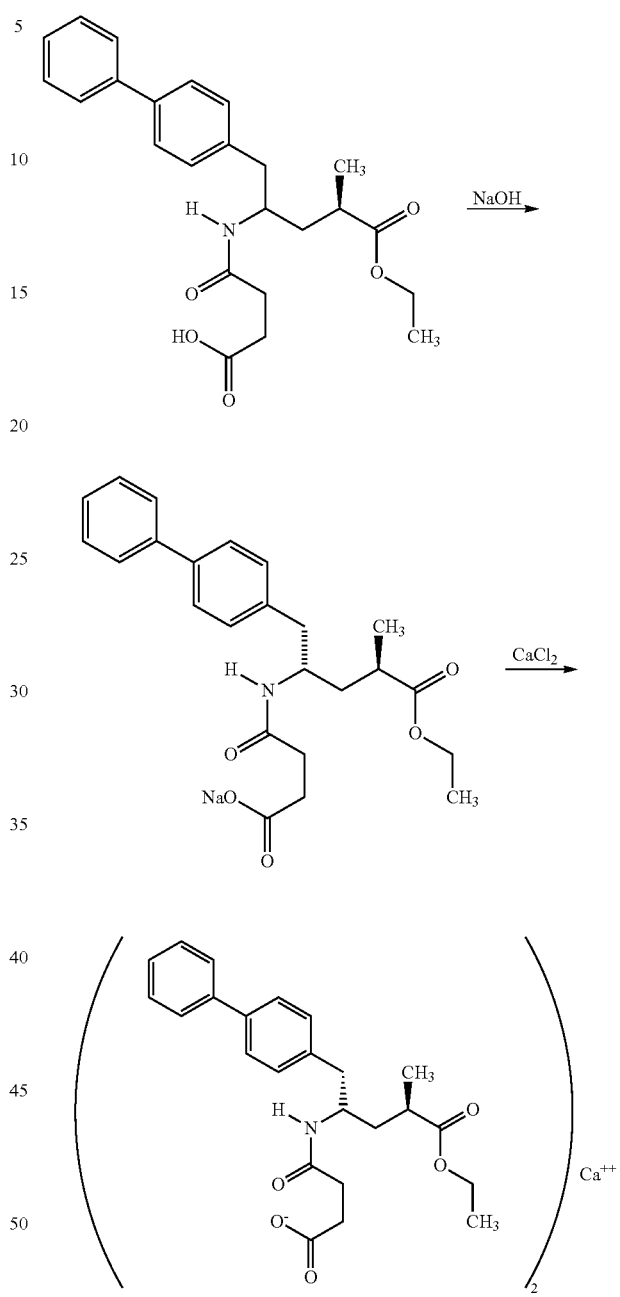

WO 2008/083967 discloses that the calcium salt is the preferred salt of N-(3-carboxyl-1-oxopropyl)-(4S)-(p-phenylphenylmethyl)-4-amino-(2R)-methyl butanoic acid ethyl ester.

The prior art does not mention any specific physical forms or processes of preparation of such forms of the calcium salt of AHU377. It is therefore a need to develop defined physical forms of the calcium salt of AHU377. Also, it is thus important to provide the calcium salt of AHU377 in a physical form which can be reliably prepared and purified on a large scale or commercial scale. That physical form should ideally be stable and not degrade on storage. The physical form chosen must also be stable whilst the drug substance is being manufactured as a formulation which is suitable for the intended route of administration chosen. In that respect, it may be necessary to consider physical properties of the physical form which lead to handling properties or higher bulk densities. In particular, non-hygroscopicity is particular important in order to obtain good flow characteristics.

The properties of the final product should also be predictable and reliably reproducible. For example, material which is obtained in an inconsistent manner, for example where the water content differs from batch to batch, must be carefully monitored. This leads to added complications in the handling, manufacture, analysis and formulation of the drug substance.

Whilst one, e.g. crystalline, form may exhibit properties which are considered suitable, another form may also have properties which, with the right measures in place, can lead to its successful development into a drug. The decision as to whether a compound is suitable for commercialization thus depends on finding a (e.g. crystalline) form of the compound which has the right balance of desirable characteristics.

Pharmaceutical formulation is affected by the rate of delivery or the bioavailability of the pharmaceutically active substance in the case of different (e.g. crystalline or amorphous) forms or polymorphs. This relationship between different forms or polymorphs and bioavailability is known in the pharmaceutical industry and across a range of pharmaceutical products.

Present inventors have directed their research work towards developing the calcium salt in advantageous forms and processes for their preparation.

SUMMARY OF THE INVENTION

In one aspect, the present invention relates to a process for preparing a crystalline or amorphous form of a calcium salt of N-(3-carboxyl-1-oxopropyl)-(4S)-(p-phenylphenylmethyl)-4-amino-(2R)-methyl butanoic acid ethyl ester (AHU377), especially of formula (I).

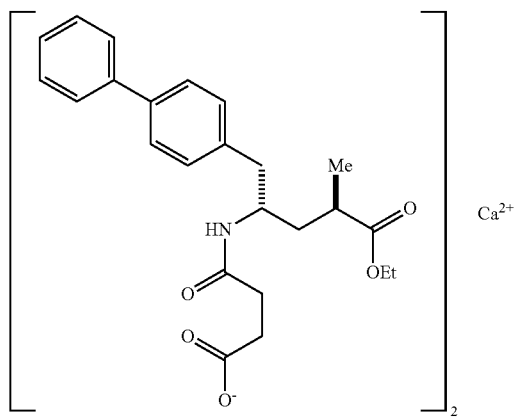

In a further aspect, there is provided a process for preparing a calcium salt of N-(3-carboxyl-1-oxopropyl)-(4S)-(p-phenylphenylmethyl)-4-amino-(2R)-methyl butanoic acid ethyl ester, especially of formula (I)

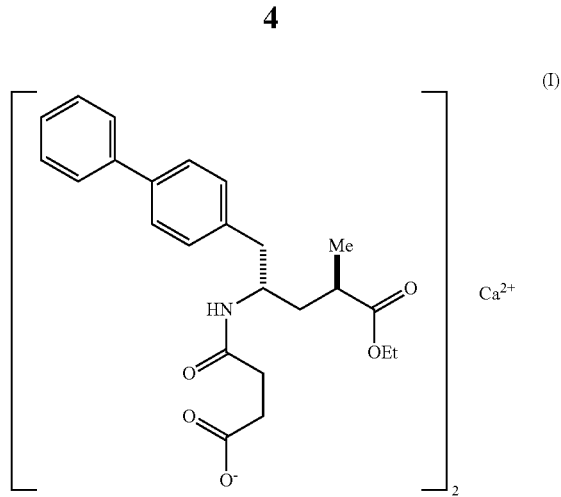

said process comprising reacting a solution of the sodium salt of N-(3-carboxyl-1-oxopropyl)-(4S)-(p-phenylphenylmethyl)-4-amino-(2R)-methyl butanoic acid ethyl ester with a calcium salt, especially a calcium halogenide, preferably $CaCl_2$.

In a further aspect, there is provided a process comprising reacting an aqueous solution of the sodium salt of N-(3-carboxyl-1-oxopropyl)-(4S)-(p-phenylphenylmethyl)-4-amino-(2R)-methyl butanoic acid ethyl ester with a solution of a calcium salt, especially a calcium halogenide, preferably $CaCl_2$, in water.

In one aspect, the present invention provides a crystalline form of the calcium salt of N-(3-carboxyl-1-oxopropyl)-(4S)-(p-phenylphenylmethyl)-4-amino-(2R)-methyl butanoic acid ethyl ester, especially of formula (I).

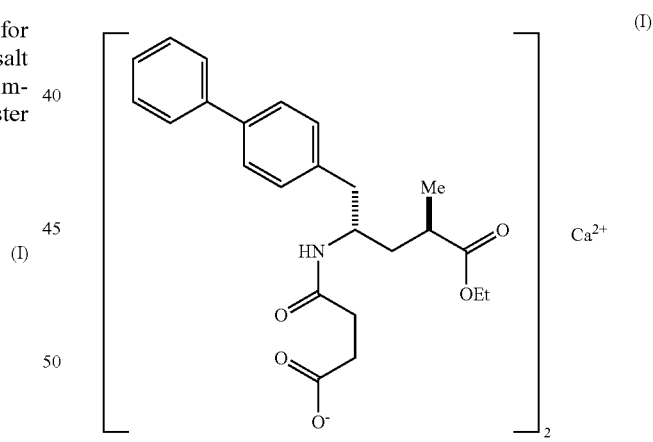

In another aspect of the invention, there is provided a process for preparing a calcium salt of N-(3-carboxyl-1-oxopropyl)-(4S)-(p-phenylphenylmethyl)-4-amino-(2R)-methyl butanoic acid ethyl ester and a calcium salt of said compound in the ratio 2:1 of N-(3-carboxyl-1-oxopropyl)-(4S)-(p-phenylphenylmethyl)-4-amino-(2R)-methyl butanoic acid ethyl ester to calcium, especially of formula (I) given above, said process comprising reacting the solution of a sodium salt of N-(3-carboxyl-1-oxopropyl)-(4S)-(p-phenylphenylmethyl)-4-amino-(2R)-methyl butanoic acid ethyl ester with a solution of a calcium salt, especially a calcium halogenide, preferably $CaCl_2$, in an aqueous solvent, such as especially water.

Embodiments of these crystalline forms of AHU377 calcium salt include those characterized herein as Modification A, Modification B (especially preferred), Modification C and Modification $H_B$ (preferred).

In a further aspect, the present invention provides an amorphous form of the calcium salt of N-(3-carboxyl-1-oxopropyl)-(4S)-(p-phenylphenylmethyl)-4-amino-(2R)-methyl butanoic acid ethyl ester of formula (I).

Each crystalline or amorphous form may be characterized by one or more or all peaks in an X-ray diffraction pattern as set forth in its corresponding Figure as mentioned below.

In another aspect of the invention, there is provided a pharmaceutical composition comprising a crystalline or amorphous form described herein, and one or more pharmaceutically acceptable carrier or excipient. The composition may comprise at least 50, 60, 70, 80 or 90 weight % of the crystalline form of the compound of formula (I), based on the weight of the compound of formula (I) in the composition. In another aspect of the invention, the pharmaceutical composition comprises an additional therapeutic agent.

The prevalence of one of the polymorphic crystalline forms can be determined by X-ray powder diffraction (XRPD) and quantitation of the characteristic signals in the XRPD spectrum.

In a further aspect, there is provided a crystalline or amorphous form or a pharmaceutical composition as described above, for use in treating or preventing conditions and disorders responsive to the inhibition of neutral endopeptidases (EC 3.4.24.11). There is also provided as one aspect of the invention the use of such crystalline form or such a pharmaceutical composition for the manufacture of a medicament for treating or preventing conditions and disorders associated with the inhibition of neutral Endopeptidase (EC 3.4.24.11).

The condition or disorder (or disease) can preferably be selected from the group consisting of hypertension, acute heart failure, chronic heart failure, congestive heart failure, left ventricular dysfunction, hypertrophic cardiomyopathy, diabetic cardiac myopathy, supraventricular and ventricular arrhythmias, atrial fibrillation, atrial flutter, detrimental vascular remodeling, myocardial infarction and its sequelae, atherosclerosis, angina (unstable or stable), renal insufficiency (diabetic and non-diabetic), heart failure, angina pectoris, diabetes, secondary aldosteronism, primary and secondary pulmonary hypertension, diabetic nephropathy, glomerulonephritis, scleroderma, glomerular sclerosis, proteinuria of primary renal disease, renal vascular hypertension, diabetic retinopathy, migraine, peripheral vascular disease, Raynaud's disease, luminal hyperplasia, cognitive dysfunction, glaucoma and stroke.

In a further aspect, there is provided a method for treating or preventing conditions and disorders associated with the inhibition of neutral endopeptidases (EC 3.4.24.11), which method comprises administering to a subject in need thereof a therapeutically effective amount of a crystalline or amorphous form, or a therapeutically effective amount of the pharmaceutical composition described herein.

In addition there is provided a process for making any one of the crystalline forms, preferably Modification B.

In addition there is provided a process for making any one of the crystalline forms, preferably Modification $H_B$.

Further aspects and embodiments of the disclosure are set forth in the following description and in the claims (which are incorporated here by reference).

DETAILED DESCRIPTION OF THE DISCLOSURE

Figure 1:
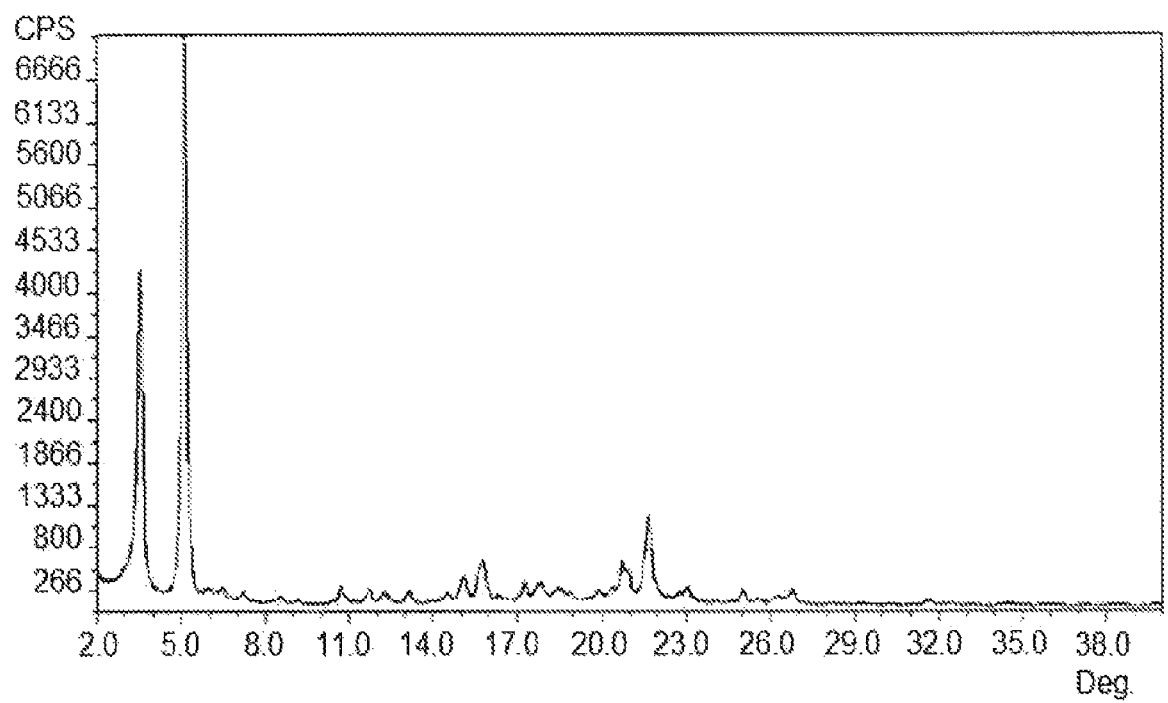
FIG. 1 illustrates the x-ray powder diffraction (XRPD) pattern of Modification A.

The invention disclosure relates to crystalline forms of the calcium salt of N-(3-carboxyl-1-oxopropyl)-(4S)-(p-phenylphenylmethyl)-4-amino-(2R)-methyl butanoic acid ethyl ester (AHU377), which are described and characterized herein.

Definitions of various terms which are used herein are listed below. The following definitions of more generic terms by more specific descriptions, as well as preceding ones, may be used to replace one, two, more or all of the generic terms in any embodiment of the invention, thus leading to more preferred invention embodiments which are all to be considered disclosed here.

As used herein "polymorph" refers to crystalline forms having the same chemical composition but different spatial arrangements of the molecules, atoms, and/or ions forming the crystal.

A particular crystalline form of the compound of formula (I) may be referred to as "crystalline form X", "crystal form X", "polymorph form X", "Modification X", or "$H_X$" where 'X' is the letter which is assigned to that particular crystalline form. Corresponding names are used herein wherein "X" is replaced by a specific symbol (letter or letter sequence).

The term "crystalline form" as used herein include reference to anhydrous crystalline forms, partially crystalline forms, mixture of crystalline forms, hydrate crystalline forms and solvate crystalline forms.

The term "hydrate" as used herein refers to a crystalline form containing one or more water molecules in a three-dimensional periodic arrangement. It can include non-stoichiometric hydrates or stoichiometric hydrates, such as hemihydrates, monohydrates, dihydrates and trihydrates.

The term "solvate" as used herein refers to a crystalline form of a molecule, atom, and/or ions that further comprises molecules of a solvent or solvents incorporated into the crystalline lattice structure. The solvent molecules in the solvate may be present in a regular arrangement and/or a non-ordered arrangement. The solvate may comprise either a stoichiometric or non-stoichiometric amount of the solvent molecules. For example, a solvate with a non-stoichiometric amount of solvent molecules may result from partial loss of solvent from the solvate. Solvates may occur as dimers or oligomers comprising more than one molecule or the calcium salt of N-(3-carboxyl-1-oxopropyl)-(4S)-(p-phenylphenylmethyl)-4-amino-(2R)-methyl butanoic acid ethyl ester (AHU377) within the crystalline lattice structure.

A hydrate is a specific variant of a solvate, and also solvates with 2 or more solvents other than water or with one or more other solvents than water in combination with water are included in the definition of "solvate" here.

The term "amorphous" as used herein refers to a solid form of a molecule, atom, and/or ions that is not crystalline. An amorphous solid does not display a definitive X-ray diffraction pattern (see for example FIG. 5).

As used herein, "substantially pure", when used in reference to a form, means a compound having a purity greater than 50, 60, 70, 80 or 90 weight %, including greater than 90, 91, 92, 93, 94, 95, 96, 97, 98, and 99 weight %, and also including equal to about 100 weight % of compound ABC, based on the weight of the compound. The remaining material comprises other form(s) of the compound, and/or reaction impurities and/or processing impurities arising from its preparation. For example, a crystalline form of the calcium salt of N-(3-carboxyl-1-oxopropyl)-(4S)-(p-phenylphenylmethyl)-4-amino-(2R)-methyl butanoic acid ethyl ester (AHU377) may be deemed substantially pure in that it has a purity greater than 90 weight %, as measured by means that are at this time known and generally accepted in the art, where the remaining less than 10% weight of material comprises other form(s) of compound ABC and/or reaction impurities and/or processing impurities. The prevalence of one of the polymorphic crystalline forms can be determined by X-ray powder diffraction (XRPD) and quantitation of the characteristic signals in the XRPD spectrum.

The term "compound of the invention" refers to a solid form of N-(3-carboxyl-1-oxopropyl)-(4S)-(p-phenylphenylmethyl)-4-amino-(2R)-methyl butanoic acid ethyl ester (AHU377) (especially represented as the compound of formula (I)), preferably any one, more or all modifications as described in the examples. It includes anhydrous crystalline forms, partially crystalline forms, mixtures of crystalline forms, hydrate crystalline forms and solvate crystalline forms.

The phrase "pharmaceutically acceptable" is employed herein to refer to those compounds, materials, compositions, and/or dosage forms which are considered suitable by a skilled person for use in contact with the tissues of human beings or animals without excessive toxicity, irritation, allergic response, or other problem or complication, commensurate with a reasonable benefit/risk ratio.

Where "substantially" is used, this means that the numeric value or other feature is essentially identical to the one mentioned after "substantially", e.g. showing a variation of ±5% of the numeric value(s), or preferably that it is identical.

Where "20 to 25° C." is used, this preferably refers to about 22° C., more preferably to 22° C.

The present invention includes all crystalline and pharmaceutically acceptable isotopically-labelled forms of the compound of formula (I). In an isotopically-labelled form, one or more atoms are replaced by an atom or atoms having the same atomic number, but an atomic mass or mass number different from the atomic mass or mass number which predominates in nature. Suitable isotopes include isotopes of hydrogen, such as $^2H$ and $^3H$; carbon, such as $^{11}C$, $^{13}C$ and $^{14}C$; nitrogen, such as $^{13}N$ and $^{15}N$; oxygen, such as $^{15}O$, $^{17}O$ and $^{18}O$. Certain isotopically-labelled compounds, such as those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds can generally be prepared by conventional techniques known to those skilled in the art or by processes analogous to those described in the accompanying examples and preparations using an appropriate isotopically-labeled reagent in place of the non-labeled reagent previously employed.

As used throughout the specification and in the claims, the term "treatment" embraces all the different forms or modes of treatment as known to those of the pertinent art and in particular includes preventive, curative, delay of progression and palliative treatment, also including treatment ameliorating patient condition with regard to one or more symptoms of a disease.

Solid State Physical Properties

Different crystalline or amorphous forms may exhibit different solid state physical properties such as hygroscopicity, behavior on compaction, stability during storage, and flowability of the solid. These properties in turn affect the suitability of a particular solid state form as an active pharmaceutical for commercial production. For example, flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate. Also compressibility and/or stability under wet granulating or dry granulating conditions are important features.

Different crystal forms or amorphous forms of the same drug may also have substantial differences in such pharmaceutically important properties as dissolution rates and bioavailability. Dissolution rates are not only a consideration in formulating syrups, elixirs and other liquid medicaments; they may also have therapeutic consequences. For example, the rate of dissolution of an active ingredient in a patient's stomach fluid can have therapeutic consequences since it imposes an upper limit on the rate at which an orally-administered active ingredient can reach the patient's bloodstream.

These practical physical characteristics are influenced by the conformation and orientation of molecules in the unit cell and/or the resulting crystal shape, which may define a particular polymorphic form of a substance. The polymorphic form may also give rise to thermal behavior different from that of the amorphous material or another polymorphic form. Thermal behavior is measured in the laboratory by such techniques as capillary melting point, thermogravimetric analysis (TGA) and differential scanning calorimetry (DSC) and can be used to distinguish some polymorphic forms from others. A particular polymorphic form may also give rise to distinct spectroscopic properties that may be detectable by single-crystal or powder X-ray crystallography, solid state $^{13}C$-NMR and $^{19}F$-NMR spectrometry and infrared spectrometry. Methods used to characterize the crystal form also include infrared spectroscopy and melting point determination.

Crystalline Forms of the Compound of Formula (I)

The present invention also provides a crystalline form of the calcium salt of AHU377, preferably a crystalline form selected from the various modifications detailed herein, preferably Modifications A, B, C and H$_B$.

In one embodiment, the crystalline form is selected from Modifications A, B, C and H$_B$. In another embodiment, the crystalline form is an anhydrous/hydrate form. In another embodiment, the crystalline form is Modification B or Modification H$_B$.

Each modification is especially characterized by its X-ray diffraction pattern with peaks as essentially depicted in the Figures or with peaks being spaced relatively to each other at the same distance (expressed as distance in 2θ) as shown in the Figures. Thus, there is provided a crystalline form selected from the various modifications detailed herein, preferably characterized in that said form has an X-ray powder diffraction pattern substantially in accordance with that shown in the corresponding Figure.

Figure 2:
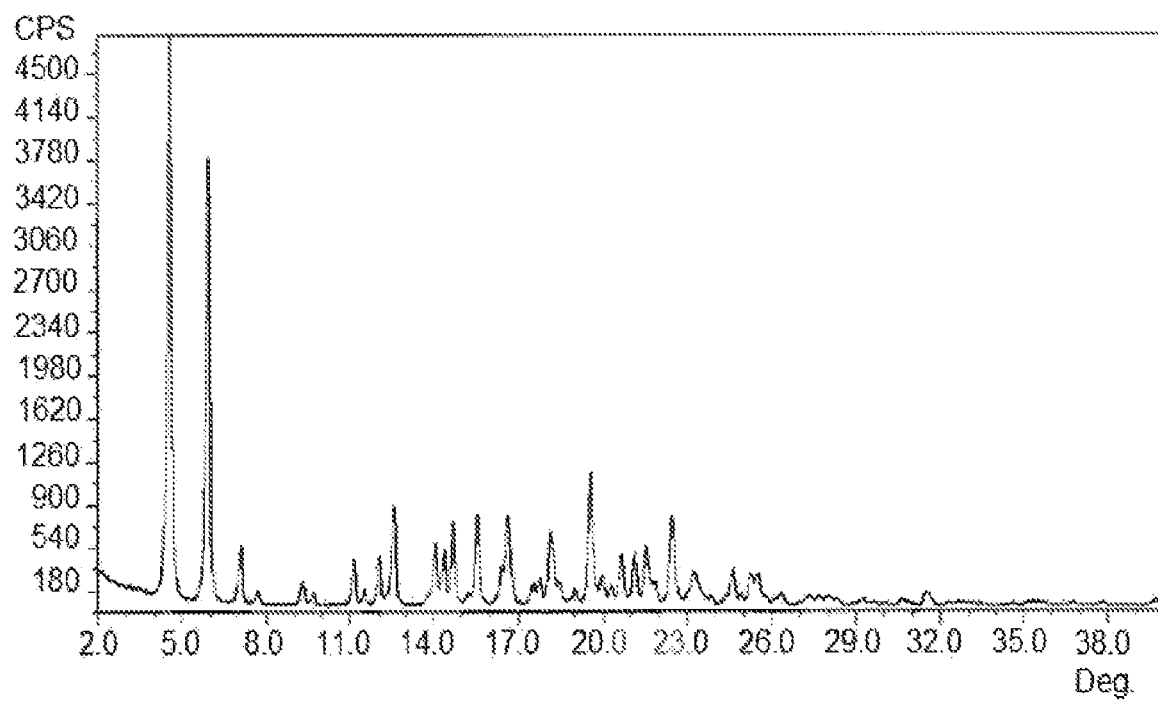
FIG. 2 illustrates the x-ray powder diffraction (XRPD) pattern of Modification B.

For instance, there is provided a crystalline form of the calcium salt of N-(3-carboxyl-1-oxopropyl)-(4S)-(p-phenylphenylmethyl)-4-amino-(2R)-methyl butanoic acid ethyl ester (AHU377) (which is preferably of formula I), in the form of Modification B, characterized by a powder X-ray diffraction pattern substantially in accordance with that shown in FIG. 2.

Alternatively, each modification is characterized by an X-ray diffraction pattern with characteristic peaks as set forth in its corresponding Table. In further embodiments, the present invention provides any of the crystalline forms of the compound of formula (I) as described herein, wherein the angle variation is ±0.3° 2θ, or ±0.2° 2θ or ±0.15° 2θ.

In further embodiments, the present invention provides any of the crystalline forms of the compound of formula (I), as described below after "for instance" or in the examples, wherein the crystalline form is characterized by a powder diffraction pattern comprising four, five or more or all 2θ values (±0.1°) (CuKα; 45 kV, 40 mA; λ=1.540598 Å) selected from a group consisting of seven 2θ values as set out under each example, at a temperature of 20 to 25° C.

For instance, there is provided a crystalline form of the calcium salt of N-(3-carboxyl-1-oxopropyl)-(4S)-(p-phenylphenylmethyl)-4-amino-(2R)-methyl butanoic acid ethyl ester (AHU377) in the form of Modification B, characterized by a powder X-ray diffraction pattern comprising 2θ values (±0.1°) (CuKα; 45 kV, 40 mA; λ=1.540598 Å) selected from the group consisting of 4.6, 6.0, 7.1, 9.3, 11.1, 12.0, 12.6, 14.0, 14.4, 14.7, 15.5, 16.6, 18.1, 19.6, 20.7, 21.1, 21.6, 22.5, 24.6, 25.3, 25.5, and 31.5 at a temperature of 20 to 25° C.

For instance, there is provided a crystalline form of the calcium salt of N-(3-carboxyl-1-oxopropyl)-(4S)-(p-phenylphenylmethyl)-4-amino-(2R)-methyl butanoic acid ethyl ester (AHU377) in the form of Modification B, characterized by a powder X-ray diffraction pattern comprising four, five, six or more 2θ values (±0.1°) (CuKα; 45 kV, 40 mA; λ=1.540598 Å) selected from the group consisting of 4.6 (particularly preferred), 6.0 (particularly preferred), 12.6, 15.5, 16.6, 18.1, 19.6 and 22.5 at a temperature of 20 to 25° C.

For instance, there is provided a crystalline form of the calcium salt of N-(3-carboxyl-1-oxopropyl)-(4S)-(p-phenylphenylmethyl)-4-amino-(2R)-methyl butanoic acid ethyl ester (AHU377) in the form of Modification B, characterized by a powder x-ray diffraction pattern comprising seven or more 2θ values (±0.1°) (CuKα; 45 kV, 40 mA; λ=1.540598 Å) selected from the group consisting of 4.6, 6.0, 12.6, 15.5, 16.6, 18.1, 19.6 and 22.5, at a temperature of 20 to 25° C.

In further embodiments, the present invention provides any of the crystalline forms of the calcium salt of AHU377, as described in the examples, wherein the crystalline form is further characterized by a powder diffraction pattern comprising five or more 2θ values (±0.1°) (CuKα; 45 kV, 40 mA; λ=1.540598 Å) selected from a group consisting of seven 2θ values as set out under each example, at a temperature of 20 to 25° C.

In further embodiments, the present invention provides any of the crystalline forms of the calcium salt of AHU377, as described in the examples, in the form of a specific modification, characterized in that said form has at least one of the following characteristics:

(a) an XRPD comprising four or more 2θ values (±0.1°) (CuKα; 45 kV, 40 mA; λ=1.540598 Å) selected from a group consisting of seven 2θ values (±0.1°, at a temperature of 20 to 25° C., as set out for each modification, or an X-ray powder diffraction pattern substantially in accordance with that shown in the Figure associated with that particular modification;

(b) a melting point, as set out for each modification in the examples section, (c) a differential thermal analysis thermogram, as set out for each modification in the examples section.

Figure 7:
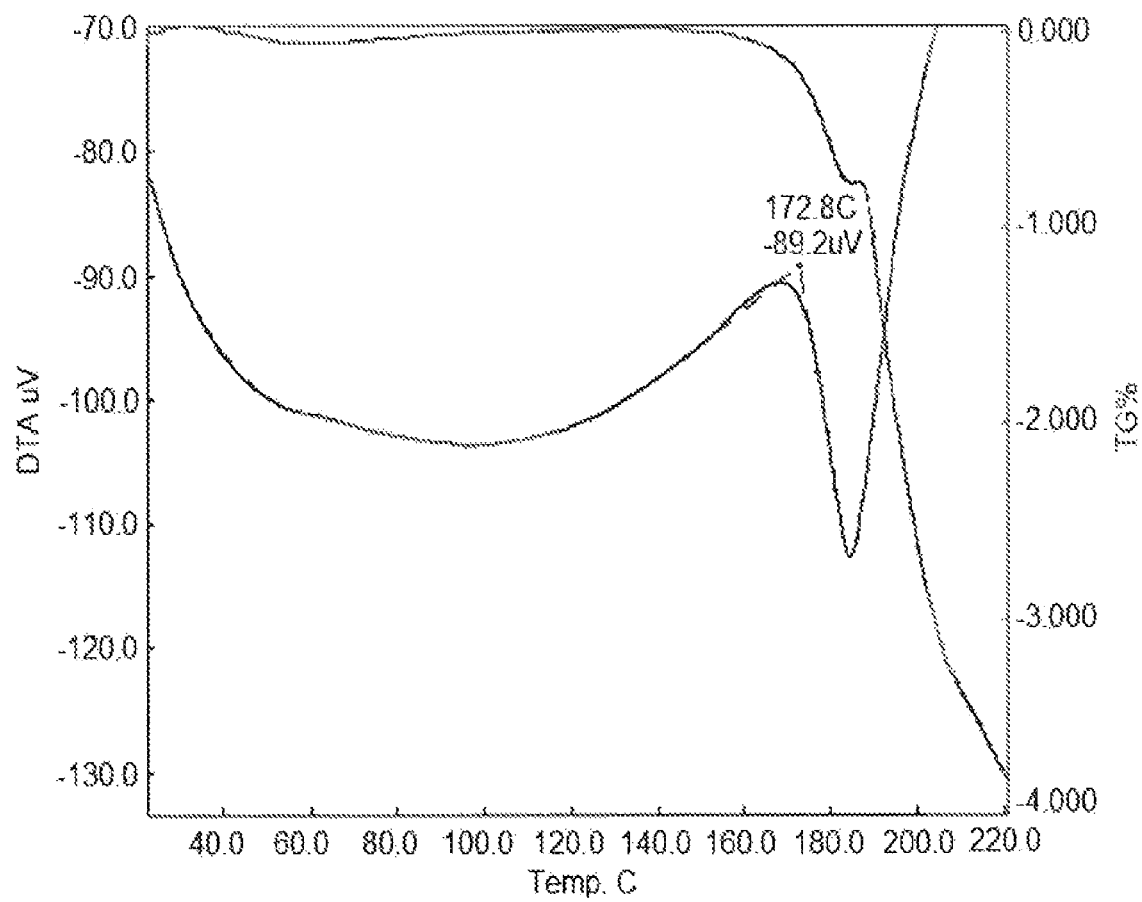
FIG. 7 illustrates the thermogravimetric analysis (TGA) of the Modification B.
Figure 8:
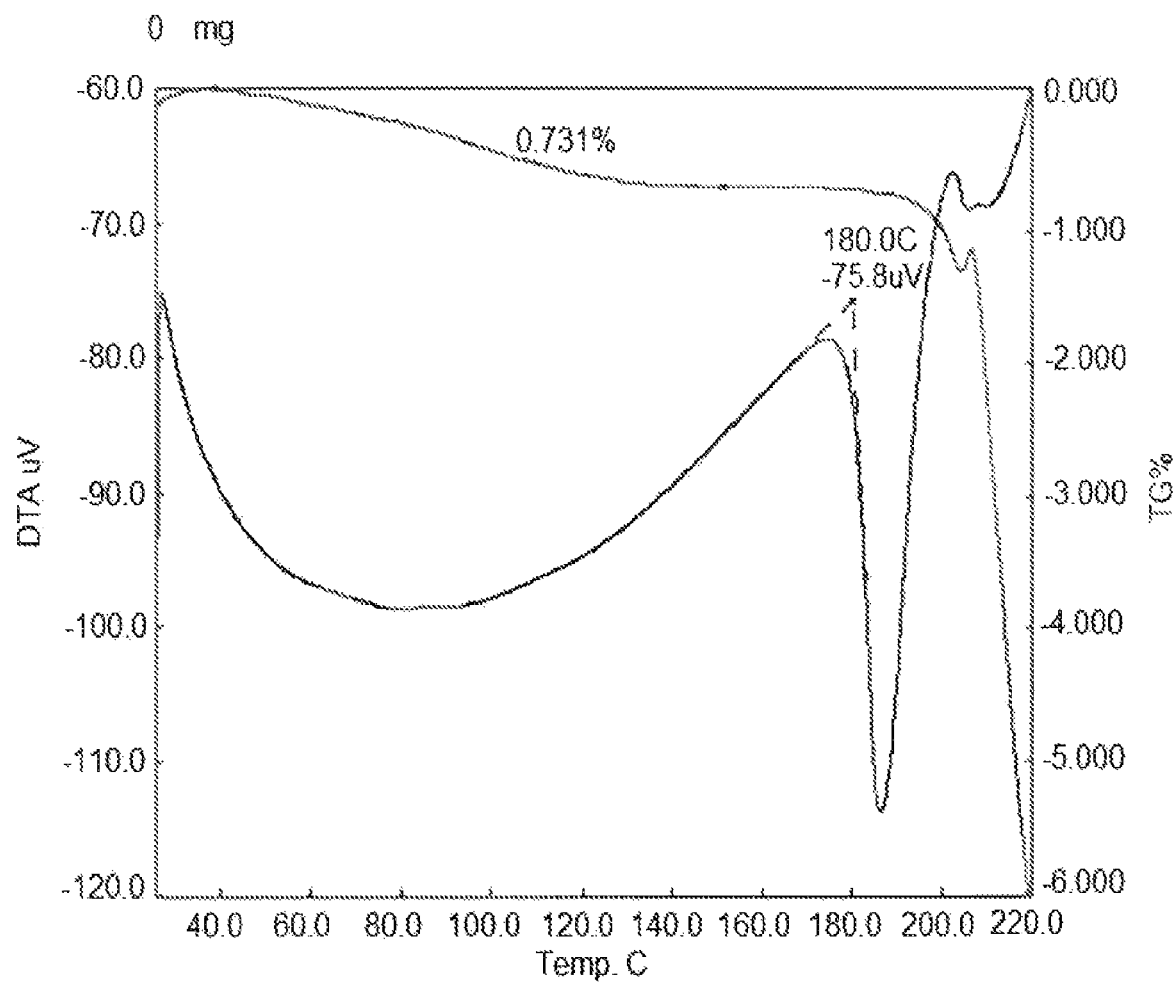
FIG. 8 illustrates the thermogravimetric analysis (TGA) of the Modification C.

Thus, for instance, there is provided a crystalline form of the calcium salt of N-(3-carboxyl-1-oxopropyl)-(4S)-(p-phenylphenylmethyl)-4-amino-(2R)-methyl butanoic acid ethyl ester (AHU377) in the form of Modification B characterized by at least one of the following characteristics:

(a) an XRPD comprising four or more 2θ values (±0.1°) (CuKα; 45 kV, 40 mA; λ=1.540598 Å) selected from the group consisting of 4.6, 6.0, 12.6, 15.5, 16.6, 18.1, 19.6 and 22.5, at a temperature of 20 to 25° C., or an X-ray powder diffraction pattern substantially in accordance with that shown in FIG. 2;

(b) a melting point with an onset at 173° C. (±2.4° C.);

(c) a differential thermal analysis thermogram with an endotherm starting at 173° C. (±2.5° C.);

(d) a thermogravimetric analysis (TGA) diagram substantially the same as that shown in FIG. 7.

In a further aspect of the invention, there is provided a form of the calcium salt of AHU377 consisting essentially of each modification, or a substantially pure form of each modification, especially of Modification B or Modification H$_B$. As used herein, "consisting essentially of each modification" or "substantially pure", when used in reference to a crystalline form, means a compound having a purity greater than 50, 60, 70, 80 or 90 weight %, including greater than 90, 91, 92, 93, 94, 95, 96, 97, 98, and 99 weight %, and also including equal to about 100 weight % of the compound of formula (I), based on the weight of the compound. The prevalence of one of the polymorphic crystalline forms can be determined by X-ray powder diffraction (XRPD) and quantitation of the characteristic signals in the XRPD spectrum. The remaining material comprises other form(s) of the compound, and/or reaction impurities and/or processing impurities arising from its preparation. For example, a crystalline form of the compound of formula (I) may be deemed substantially pure in that it has a purity greater than 90 weight %, as measured by means that are at this time known and generally accepted in the art, where the remaining less than 10 weight % of material comprises other form(s) of the compound of formula (I) and/or reaction impurities and/or processing impurities.

In other embodiments, there is provided a crystalline form comprising at least 80, 85, 90, 95 or 99 weight % of the modification of interest.

There is also provided a crystalline form comprising at least 95 or 99 weight % of the modification of interest. Thus, for instance, there is provided a crystalline form comprising at least 95 or 99 weight % of each of the preferred modifications, especially Modification B.

For instance, there is provided a crystalline form of the calcium salt of N-(3-carboxyl-1-oxopropyl)-(4S)-(p-phenylphenylmethyl)-4-amino-(2R)-methyl butanoic acid ethyl ester (AHU377) in the form of Modification $H_B$, characterized by a powder X-ray diffraction pattern comprising 2θ values (±0.1°) (CuKα; 45 kV, 40 mA; λ=1.540598 Å) selected from the group consisting of 3.6, 6.1, 6.4, 7.6, 8.4, 10.8, 11.3, 12.8, 14.6, 15.3, 16.8, 17.8, 19.7, 20.6, 21.4, 22.5, 23.4 and 24.8 at a temperature of 20 to 25° C.

For instance, there is provided a crystalline form of the calcium salt of N-(3-carboxyl-1-oxopropyl)-(4S)-(p-phenylphenylmethyl)-4-amino-(2R)-methyl butanoic acid ethyl ester (AHU377) in the form of Modification $H_B$, characterized by a powder X-ray diffraction pattern comprising four, five, six or more 2θ values (±0.1°) (CuKα; 45 kV, 40 mA; λ=1.540598 Å) selected from the group consisting of 3.6, 6.4, 8.4, 14.6, 15.3, 16.8, 17.8, 19.7 and 20.6 at a temperature of 20 to 25° C.

For instance, there is provided a crystalline form of the calcium salt of N-(3-carboxyl-1-oxopropyl)-(4S)-(p-phenylphenylmethyl)-4-amino-(2R)-methyl butanoic acid ethyl ester (AHU377) in the form of Modification $H_B$, characterized by a powder x-ray diffraction pattern comprising seven or more 2θ values (±0.1°) (CuKα; 45 kV, 40 mA; λ=1.540598 Å) selected from the group consisting of 3.6, 6.4, 8.4, 14.6, 15.3, 16.8, 17.8, 19.7 and 20.6, at a temperature of 20 to 25° C.

In further embodiments, the present invention provides any of the crystalline forms of the calcium salt of AHU377, as described in the examples, wherein the crystalline form is further characterized by a powder diffraction pattern comprising five or more 2θ values (±0.1°) (CuKα; 45 kV, 40 mA; λ=1.540598 Å) selected from a group consisting of seven 2θ values as set out under each example, at a temperature of 20 to 25° C.

Thus, for instance, there is provided a crystalline form of the calcium salt of N-(3-carboxyl-1-oxopropyl)-(4S)-(p-phenylphenylmethyl)-4-amino-(2R)-methyl butanoic acid ethyl ester (AHU377) in the form of Modification $H_B$ characterized in that said form has at least one of the following characteristics:
(a) comprising four or more 2θ values (±0.1°) (CuKα; 45 kV, 40 mA; λ=1.540598 Å) selected from the group consisting of 3.6, 6.4, 8.4, 14.6, 15.3, 16.8, 17.8, 19.7 and 20.6, at a temperature of 20 to 25° C., or an X-ray powder diffraction pattern substantially in accordance with that shown in FIG. 4;
(b) a melting point with an onset at 180° C. (±2.4° C.);
(c) a differential thermal analysis thermogram with an endotherm starting at 180° C. (±2.5° C.).

For instance, there is provided a crystalline form of the crystalline form of the calcium salt of N-(3-carboxyl-1-oxopropyl)-(4S)-(p-phenylphenylmethyl)-4-amino-(2R)-methyl butanoic acid ethyl ester (AHU377) in the form of Modification A, characterized by a powder X-ray diffraction pattern comprising 2θ values (±0.1°) (CuKα; 45 kV, 40 mA; λ=1.540598 Å) selected from the group consisting of 3.6, 5.1, 10.7, 11.7, 12.2, 13.1, 15.1, 15.8, 17.3, 17.8, 20.7, 21.7, 23.0, 25.0 and 26.8 at a temperature of 20 to 25° C.

For instance, there is provided a crystalline form of the crystalline form of the calcium salt of N-(3-carboxyl-1-oxopropyl)-(4S)-(p-phenylphenylmethyl)-4-amino-(2R)-methyl butanoic acid ethyl ester (AHU377) in the form of Modification A, characterized by a powder X-ray diffraction pattern comprising four, five, six or more 2θ values (±0.1°) (CuKα; 45 kV, 40 mA; λ=1.540598 Å) selected from the group consisting of 3.6, 5.1, 15.1, 15.8, 17.3, 17.8, 20.7 and 21.7 at a temperature of 20 to 25° C.

For instance, there is provided a crystalline form of the calcium salt of N-(3-carboxyl-1-oxopropyl)-(4S)-(p-phenylphenylmethyl)-4-amino-(2R)-methyl butanoic acid ethyl ester (AHU377) in the form of Modification A, characterized by a powder X-ray diffraction pattern comprising seven or more 2θ values (±0.1°) (CuKα; 45 kV, 40 mA; λ=1.540598 Å) selected from the group consisting of 3.6, 5.1, 15.1, 15.8, 17.3, 17.8, 20.7 and 21.7, at a temperature of 20 to 25° C.

In further embodiments, the present invention provides any of the crystalline forms of calcium salt of N-(3-carboxyl-1-oxopropyl)-(4S)-(p-phenylphenylmethyl)-4-amino-(2R)-methyl butanoic acid ethyl ester (AHU377), as described in the examples, wherein the crystalline form is further characterized by a powder diffraction pattern comprising five or more 2θ values (±0.1°) (CuKα; 45 kV, 40 mA; λ=1.540598 Å) selected from a group consisting of seven 2θ values as set out under each example, at a temperature of about 22° C.

For instance, there is provided a crystalline form of the calcium salt of N-(3-carboxyl-1-oxopropyl)-(4S)-(p-phenylphenylmethyl)-4-amino-(2R)-methyl butanoic acid ethyl ester (AHU377) in the form of Modification A characterized by at least one of the following characteristics:
(a) comprising four or more 2θ values (±0.1°) (CuKα; 45 kV, 40 mA; λ=1.540598 Å) selected from the group consisting of 3.6, 5.1, 15.1, 15.8, 17.3, 17.8, 20.7 and 21.7 at a temperature of about 22° C., or an X-ray powder diffraction pattern substantially in accordance with that shown in FIG. 1;
(b) a melting point with an onset at 192° C. (±2.4° C.);
(c) a differential thermal analysis thermogram with an endotherm starting at 192° C. (±2.5° C.).

For instance, there is provided a crystalline form of the crystalline form of the calcium salt of N-(3-carboxyl-1-oxopropyl)-(4S)-(p-phenylphenylmethyl)-4-amino-(2R)-methyl butanoic acid ethyl ester (AHU377) in the form of Modification C, characterized by a powder X-ray diffraction pattern comprising 2θ values (±0.1°) (CuKα; 45 kV, 40 mA; λ=1.540598 Å) selected from the group consisting of 4.6, 6.2, 14.5, 15.4, 20.4, 21.7 and 22.1 at a temperature of 20 to 25° C.

For instance, there is provided a crystalline form of the crystalline form of the calcium salt of N-(3-carboxyl-1-oxopropyl)-(4S)-(p-phenylphenylmethyl)-4-amino-(2R)-methyl butanoic acid ethyl ester (AHU377) in the form of Modification C, characterized by a powder x-ray diffraction pattern comprising four, five, six or more 2θ values (±0.1°) (CuKα; 45 kV, 40 mA; λ=1.540598 Å) selected from the group consisting of 4.6, 6.2, 14.5, 15.4, 20.4, 21.7 and 22.1 at a temperature of 20 to 25° C.

For instance, there is provided a crystalline form of the calcium salt of N-(3-carboxyl-1-oxopropyl)-(4S)-(p-phenylphenylmethyl)-4-amino-(2R)-methyl butanoic acid ethyl ester in the form of Modification C, characterized by a powder X-ray diffraction pattern comprising seven 2θ values (±0.1°) (CuKα; 45 kV, 40 mA; λ=1.540598 Å) selected from the group consisting of 4.6, 6.2, 14.5, 15.4, 20.4, 21.7 and 22.1 at a temperature of 20 to 25° C.

Figure 3:
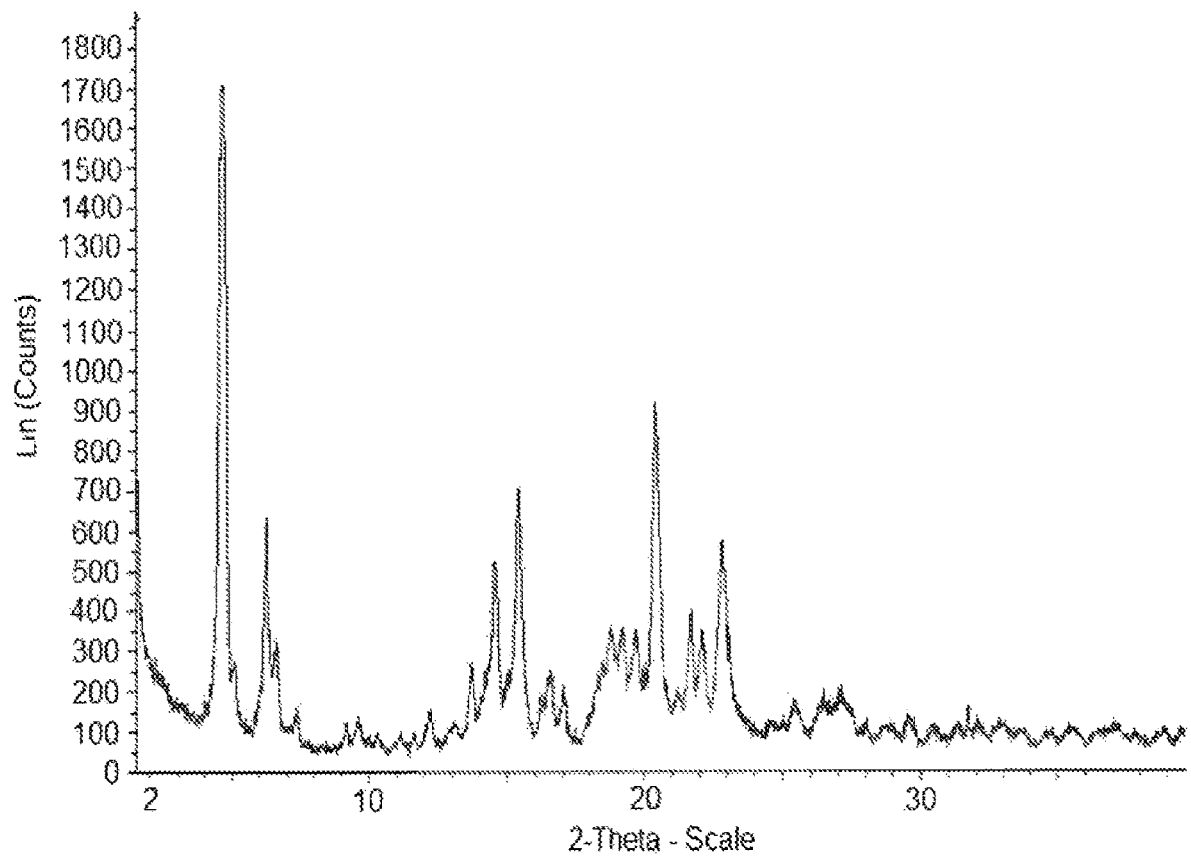
FIG. 3 illustrates the x-ray powder diffraction (XRPD) pattern of Modification C.

Thus, for instance, there is provided a crystalline form of the calcium salt of N-(3-carboxyl-1-oxopropyl)-(4S)-(p-phenylphenylmethyl)-4-amino-(2R)-methyl butanoic acid ethyl ester in the form of Modification C characterized by at least one of the following characteristics:

(a) comprising four or more 2θ values (±0.1°) (CuKα; 45 kV, 40 mA; λ=1.540598 Å) selected from the group consisting of 4.6, 6.2, 14.5, 15.4, 20.4, 21.7 and 22.1 at a temperature of 20 to 25° C., or an X-ray powder diffraction pattern substantially in accordance with that shown in FIG. 3;

(b) a melting point with an onset at 180° C. (±2.4° C.);

(c) a differential thermal analysis thermogram with an endotherm starting at 180° C. (±2.5° C.).

For instance, there is provided an amorphous form of the calcium salt of N-(3-carboxyl-1-oxopropyl)-(4S)-(p-phenylphenylmethyl)-4-amino-(2R)-methyl butanoic acid ethyl ester, characterized by a powder X-ray diffraction pattern comprising 2θ values (±0.1°) (CuKα; 45 kV, 40 mA; λ=1.540598 Å) of 3.7 at a temperature of 20 to 25° C.

Figure 5:
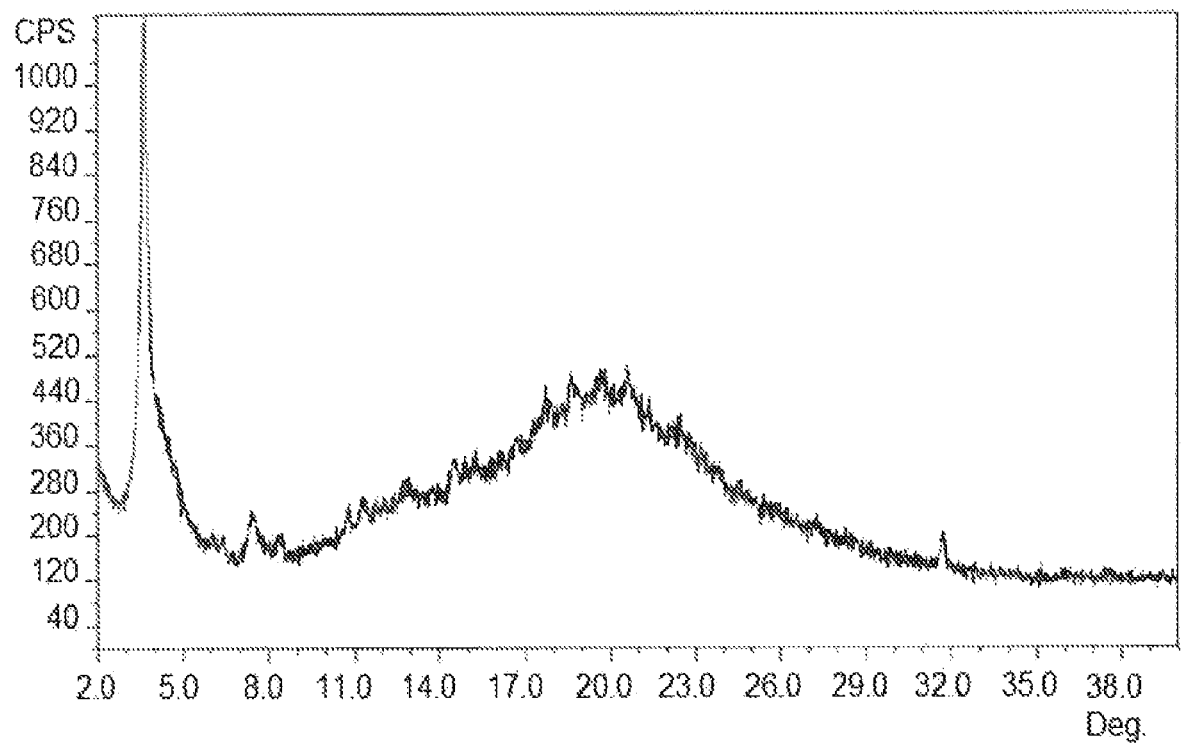
FIG. 5 illustrates the x-ray powder diffraction (XRPD) pattern of the amorphous calcium salt of AHU377.
Figure 6:
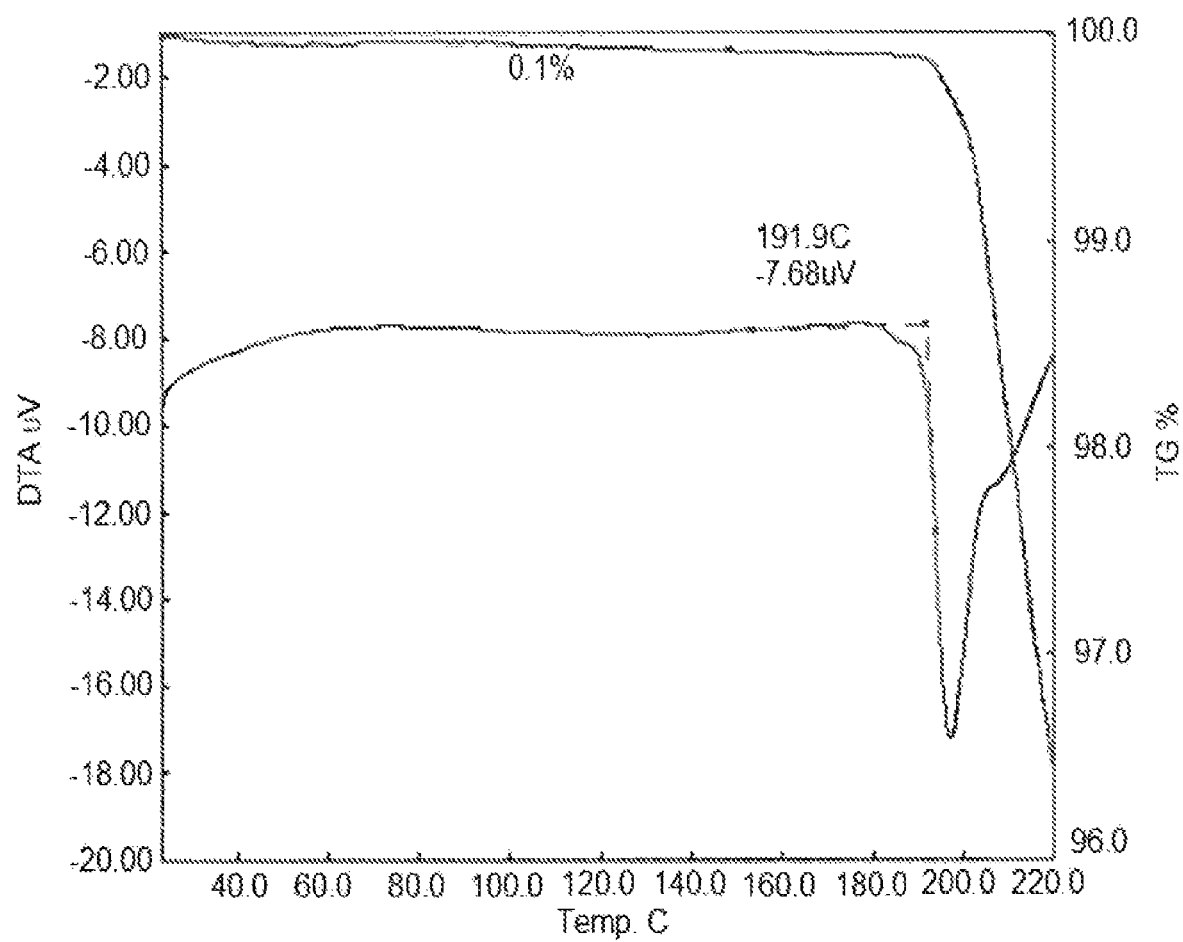
FIG. 6 illustrates the thermogravimetric analysis (TGA) of the Modification A.

Thus, for instance, there is provided amorphous form of the calcium salt of N-(3-carboxyl-1-oxopropyl)-(4S)-(p-phenylphenylmethyl)-4-amino-(2R)-methyl butanoic acid ethyl ester characterized in that said form has at least one of the following characteristics:

(a) powder x-ray diffraction pattern comprising 2θ values (±0.1°) (CuKα; 45 kV, 40 mA; λ=1.540598 Å) of 3.7 at a temperature of 20 to 25° C., or an X-ray powder diffraction pattern substantially in accordance with that shown in FIG. 5 without characteristic peaks;

(b) a melting point with an onset at 204° C. (±2.4° C.);

(c) a differential thermal analysis thermogram with an endotherm starting at 204° C. (±2.5° C.).

Preparation of Crystalline Forms of the Calcium Salt of AHU377

In a further aspect, the present invention provides a process to make the calcium salt of AHU377 Modification $H_B$ starting from AHU377 alkaline metal salt, e.g. sodium salt.

In a further aspect, the present invention provides a process to produce Modification B starting from Modification $H_B$, or the use of Modification $H_B$ for producing Modification B.

The present invention provides a process for making the calcium salt of AHU377 Modification B starting from AHU377 Modification $H_B$.

In a further aspect, the present invention provides a process to produce Modification B from the calcium salt of AHU377.

In a further aspect, the present invention provides a process to produce Modification A starting from the amorphous calcium salt of AHU377, or the use of the amorphous calcium salt of AHU377 to produce Modification A.

In a further aspect, the present invention provides a process to make Modification C starting from the amorphous calcium salt of AHU377, or the use of the amorphous calcium salt of AHU377 to produce Modification C.

In a further aspect, the present invention provides a process to make the amorphous calcium salt of AHU377 starting from the sodium salt of AHU377, or the use of the sodium salt of AHU377 to produce the amorphous calcium salt of AHU377.

In a further aspect, the present invention provides the use of any of the crystalline forms described herein, to produce another crystalline form. Preferably, Modification $H_B$ is used to produce another crystalline form, more preferably, to produce Modification B.

The present invention also provides a process for the preparation of Modification B wherein a calcium salt of AHU377, especially the compound of formula (I), e.g. in the form of Modification $H_B$, is dispersed or slurried in a solvent system, the resulting mixture is heated to reflux, cooled and seed crystals of Modification B are added, the suspension is stirred, the solid obtained is filtered and the residue obtained after filtration is dried.

Alternatively, the solvent system may be a single solvent system, wherein the solvent includes ethanol; preferably it is absolute ethanol, or further heptane or 2-propanol.

Modification B may also be obtained using a process wherein crystallization of AHU377 from a clear solution is used to prepare Modification B. This has the major advantage to directly allow to comply with requirements imposed by some drug regulatory authorities, e.g. the Food Drug Agency's Good Manufacturing Practices (GMP) requirements, in that a clarifying filtration from a clear solution is carried out in the drug substance production step itself, in order to remove any insoluble particles.

The same filtration can be made before the crystallization of any other of the Modifications of AHU377 calcium salt mentioned herein.

The present invention thus also provides a process for the preparation of Modification B using a recrystallization method comprising the steps of (a) dissolving the compound of formula (I) in a solvent, preferably ethanol (b) heating the reaction mixture to a temperature between 60° C. and reflux temperature, (c) cooling the reaction mixture to 40 to 80, e.g. 50±5° C.;

(d) optionally adding Modification B seed crystals;

(e) optionally (or preferably) stirring the reaction mixture, preferably for at least 12 hours;

(f) filtering solid from the mixture obtained at the end of step (c), (d) or (e); and (g) optionally drying the crystals.

The present invention also provides a process for the preparation of Modification $H_B$ using a crystallization and recrystallization method comprising the steps of (a) concentrating the solution of the sodium salt of AHU377 in a solvent system by heating the reaction mixture under reduced pressure, wherein said solvent system is water;

(b) diluting the reaction mixture with water (c) heating the reaction mixture to 65 to 95° C., e.g. 83±5° C.;

(d) adding a solution of calcium chloride in water;

(e) stirring the reaction mixture for at least 4.5 h at 65 to 95° C., e.g. 83±5° C.;

(f) cooling the reaction mixture to 65±5° C.;

(g) heating the reaction mixture to 65 to 95° C., preferably 83±5° C.;

(h) repeating the cycles for at least three times;

(i) cooling the reaction mixture to at least 40 to 80, e.g. 50±5° C.;

(j) filtering the mixture obtained at the end of step (h);

(k) optionally drying the crystals.

The present invention thus also provides a process for the preparation of Modification $H_B$ using a crystallization and recrystallization method comprising the steps of (a) heating the solution of the sodium salt of AHU377 in a solvent system, wherein said solvent system is water;

(b) adding isopropyl acetate to the reaction mixture;

(c) heating the reaction mixture to 65 to 95° C., e.g. 83±5° C.;

(d) adding a solution of calcium chloride in water;

(e) stirring the reaction mixture (e.g. for at least 15 h) to 50±5° C.;

(f) filtering the mixture obtained at the end of step (e);

(g) suspending the solid obtained in step (f) in solvent system, wherein said solvent system is water and isopropyl acetate;
(h) stirring the reaction mixture (e.g. for at least 20 min) to 40 to 80° C., e.g. 50±5° C.;
(i) filtering the mixture obtained at the end of step (h);
(j) suspending the solid obtained in step (i) in solvent system, wherein said solvent system is water;
(k) stirring the reaction mixture for at least 20 min to 40 to 80° C., e.g. 50±5° C.;
(l) filtering the mixture obtained at the end of step (k);
(m) optionally drying the crystals.

Administration and Pharmaceutical Formulations

The compound(s) of the invention will normally be administered orally, intravenously, subcutaneously, buccally, rectally, dermally, nasally, tracheally, bronchially, by any parenteral route, as an oral or nasal spray or via inhalation. Parenteral modes of administration include intravenous, intramuscular, intraperitoneal, intrasternal, subcutaneous and intraarticular injections and infusions. Pharmaceutical compositions suitable for the delivery of the compound(s) of the invention and methods for their preparation may be found, e.g. *Remington's Pharmaceutical Sciences,* 19$^{th}$ Edition, Mack Publishing Company, 1995.

The compound(s) of the invention may be administered orally. Advantageously, the compound(s) of the invention may be orally active, have rapid onset of activity and low toxicity. Oral administration may involve swallowing, so that the compound enters the gastrointestinal tract, or buccal or sublingual administration may be employed by which the compound enters the blood stream directly from the mouth.

Examples of formulations suitable for oral administration are solid formulations such as tablets, capsules containing particulates, liquids, or powders, lozenges (including liquid-filled), chews, multi- and nano-particulates, gels, solid solution, liposome, films, ovules, sprays and liquid formulations.

Examples of liquid formulations include suspensions, solutions, syrups and elixirs. These may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, and salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

The compounds may be administered alone or as compositions in combination with pharmaceutically acceptable diluents, excipients or carriers. The present invention thus provides a pharmaceutical composition comprising a therapeutically effective amount of a compound of the invention, alone or in combination with one or more pharmaceutically acceptable carriers (excipients). Combination partners may e.g. be selected from angiotensin receptor blockers (ARBs), preferably an ARB selected from the group consisting of losartan, irbesartan, candesartan, eprosartan, telmisartan, olmesartan and valsartan, preferably valsartan, or pharmaceutically acceptable salts thereof.

Most preferably the compound AHU377 (sacubitril) can be part of a complex with valsartan, especially as octadecasodium hexakis(4-{[(1S,3R)-1-([1,1'-biphenyl]-4-ylmethyl)-4-ethoxy-3-methyl-4-oxobutyl]amino}-4-oxobutanoate) hexakis(N-pentanoyl-N-{[2'-(1H-tetrazol-1-id-5-yl)[1,1'-biphenyl]-4-yl]methyl}-L-valinate)-water (1/15), which may be synthesized according to and is disclosed in WO 2007/056546 A1. The present AHU377 calcium salts can be used advantageously to prepare this complex.

The compounds of the invention, e.g. any one of the various modifications, e.g. crystalline forms, may be used alone or in combination, or formulated with one or more carriers or excipients or other active pharmaceutical ingredients to provide formulations suitable for the treatment of the indications identified above.

Examples of such carriers or excipients include but are not limited to any one or more of:
a) a diluent, e.g., lactose, dextrose, sucrose, mannitol, sorbitol, cellulose and/or glycine;
b) a lubricant, e.g., silica, talcum, stearic acid, its magnesium or calcium salt and/or polyethylene glycol;
c) a binder, e.g., magnesium aluminum silicate, starch paste, gelatin, tragacanth, methylcellulose, sodium carboxymethylcellulose and or polyvinylpyrrolidone;
d) a disintegrant, e.g., starches, agar, alginic acid or its sodium salt, or effervescent mixtures; and
e) an absorbant, a colorant, a flavor and/or a sweetener.

Additional examples of useful excipients are described in the *Handbook of pharmaceutical excipients,* 3rd edition, edited by A. H. Kibbe, published by the American Pharmaceutical Association, Washington D.C., ISBN: 0-917330-96-X, or *Handbook of Pharmaceutical Excipients* (4$^{th}$ edition), edited by Raymond C. Rowe, published by Science and Practice which are incorporated herewith by reference or simply provided as basis for reference.

Depending upon the disorder and patient to be treated and the route of administration, the composition(s) may be administered at equal or varying doses. In general, the daily dose range of a compound of the invention lies within the range of from about 0.0001 mg/kg to about 100 mg/kg, preferably from about 0.001 mg/kg to about 50 mg/kg body weight of a subject in single or divided doses. On the other hand, it may be necessary to use dosages outside these limits in some cases.

In the case where an oral composition is employed, a suitable dosage range of a compound of the invention is, e.g. from about 0.001 mg/kg to about 100 mg/kg body weight of a subject in the composition per day, preferably from about 0.01 mg to about 2000 mg per day. For oral administration, the compositions are preferably provided in the form of tablets containing from 0.01 mg to 2000 mg, e.g. 0.01, 0.05, 0.1, 0.2, 0.5, 1.0, 2.5, 5, 10, 15, 20, 25, 30, 40, 50, 75, 80 mg.

In one embodiment, a compound of the invention is used/is formulated at a dose of 1 to 2000 mg, 1 to 1000 mg, 2 to 500 mg, 5-500 mg, of 10-400 mg, or of 20-300 mg. In another embodiment, the NEP inhibitor is used at a dose of 5, 10, 15, 20, 25, 30 40, 50, 100 or 200 mg. In a preferred embodiment, the NEP inhibitor is used at a dose of 50, 100, or 200 mg, based on the amount of the compound of formula (I).

It is to be understood that the doses quoted herein refer to the NEP inhibitor in the free form (not as a salt). When a pharmaceutically acceptable salt of the NEP inhibitor is used, the doses used will need to be adjusted accordingly.

The present invention further provides a pharmaceutical composition, preferably a tablet or a gelatin capsule, as herein described, comprising a second active ingredient (i.e. combination partner) as described below in the 'Combination therapy' section.

Accordingly, the present invention provides a pharmaceutical composition as described herein as for use as a medicament. A pharmaceutical composition as described herein is also provided for use in the treatment of a disorder or a condition associated with NEP inhibition activity. A pharmaceutical composition as described therein for the manufacture of a medicament for the treatment of a disorder or a condition associated with NEP inhibition activity is also provided.

A method of preventing or treating a disorder or a condition associated with NEP inhibition activity comprising administrating a therapeutically effective amount of the composition to a subject in need of such a treatment is also provided.

Use

As described herein above, the compounds of the present invention may be useful for the treatment or prevention of a disorder or a condition mediated by NEP inhibition activity in animals, particularly humans.

Thus the present invention also provides a method for treating or preventing a condition or a disorder associated with NEP inhibition activity, which method comprises administering a therapeutically effective amount of a compound of the invention to a subject in need thereof.

Thus the present invention provides the use of a compound of the invention, alone or in combination with another therapeutic agent (see below) for the manufacture of a medicament for treating or preventing a conditions or a disorder associated with NEP inhibition activity in animals, particularly humans. A compound of the invention, alone or in combination with another therapeutic agent (see below), is also provided for use in treating or preventing a condition or a disorder associated with NEP inhibition activity in animals, particularly humans.

EXAMPLES

The following examples illustrate the invention without limiting its scope.

The following abbreviations are used herein.

| L | Liter |
| LOD | Loss on drying |
| mL | milliliter |
| r.h. or RH | Relative humidity |
| TG/DTA | Thermogravimetric/differential thermal analysis |
| VTGA | Vacuum thermogravimetric analysis |

Other abbreviations used are those conventional in the art.
Methodology, Instruments and Standards Used
(i) X-Ray Powder Diffraction (XRPD)

The X-ray powder diffraction pattern was determined using a Scintag XDS 2000 diffractometer instrument. The X-ray diffraction pattern was recorded between 2° and 35° (2θ) with CuK radiation (45 kV, 40 mA). The measurements were performed at about 45 kV and 40 mA under the following conditions:

Scan rate: 0.5° (2θ)/min
Chopper increment: 0.02°
Slits (from left to right): 2, 3, 0.3, 0.2 mm
The spectra were recorded in the reflection mode.

| XRPD method |
|---|
| Instrument: XDS 2000; Scintag Inc., Cupertino, CA, USA |
| Irradiation: CuK (45 kV, 40 mA) |
| CuK$_\alpha$ = 1.540598 Å |
| Scan range: 2-40° (2θ value) |
| Scan type: Continuous scan |
| Step time: 180 seconds |
| Step size: 0.02° |
| Temperature: 20° C. to 25° C. |

XRPD profiles for the respective solid forms are shown in the figures.

Characteristic peaks of compounds of the invention are listed herein in the tables below and described in the figures. The peaks listed herein are given in degrees 2θ (±0.2°, preferably ±0.1°).

As will be appreciated by the skilled person, the relative intensities of the various peaks within the tables given below may vary due to a number of factors such as for example orientation effects of crystals in the X-ray beam or the purity of the material being analyzed or the degree of crystallinity of the sample. The peak positions may also shift for variations in sample height but the peak positions will remain substantially as defined in given tables. The skilled person will also appreciate that measurements using a different wavelength will result in different shifts according to the Bragg equation −nλ=2d sin θ. Such alternative XRPD patterns generated by use of alternative wavelengths are nevertheless representations of the same material.

(ii) Thermogravimetric/Differential Thermal Analysis (TG/DTA)

Differential scanning calorimetry was conducted for each crystalline form using a Seiko TG/DTA Instrument. For each analysis, the DSC cell/sample chamber was purged with 100 mL/min of ultra-high purity nitrogengas. The instrument was calibrated with high purity indium. The heating rate was 10° C. per minute in the temperature range between 25 and 300° C. The heat flow, which was normalized by sample weight, was plotted versus the measured sample temperature. The data were reported in units of watts/gram ("W/g"). The plot was made with the endothermic peaks pointing down. The endothermic melt peak (melting point) was evaluated for extrapolated onset temperature.

| TG/DTA-method | |
|---|---|
| Instrument | Seiko TG/DTA |
| Temperature range | 20-260° C. |
| Scan rate | 10° C./min |
| Nitrogen flow | 100 mL/min |

As used herein, the terms "a concentration of a given modification in a given solvent (X), another solvent (Y) is added" means the solution obtained after the given modification is dissolved in the former solvent (X) to a high concentration (>75 mg/ml) and the latter solvent (Y) is added to initiate crystallization.

Example 1: Calcium salt of N-(3-carboxyl-1-oxopropyl)-(4S)-(p-phenylphenylmethyl)-4-amino-(2R)-methyl butanoic acid ethyl ester (Calcium Salt of AHU377)

To a mixture of AHU377 free acid (17.7 g) in isopropyl acetate (190 mL), solid sodium hydroxide (1.9 g) is added, thus yielding AHU377 sodium salt which is directly used for manufacture of the calcium salt. The mixture is stirred at 25° C. for 70 min to give a turbid mixture. Addition of solid calcium chloride (2.4 g) is followed by seeding with AHU377 Modification B (obtainable e.g. as described in Example 2) at room temperature. The white suspension is stirred at 25° C. for 20 h, then filtered and washed with isopropyl acetate to give solid AHU377 calcium salt after drying at 50° C. under reduced pressure.

Example 2: Modification B

AHU377 calcium salt (2500 g) from Example 3, 7 or 8 is suspended in absolute ethanol (60 L) at room temperature. The reaction mixture is heated to 78° C. (reflux) over 30 min, then further stirred at this temperature for 30 min before being cooled to 50° C. over 30 min. Seed crystals of Modification B (2 g) are added, and the suspension is stirred for 12-18 h. The solids are filtered at 50° C., washed with absolute ethanol (9.5 L), and dried at 60° C. under reduced pressure to give AHU377 calcium salt, Modification B.

When characterized by X-ray powder diffraction, Modification B gives the pattern shown in FIG. 2. The characteristic peaks (±0.1°) are given in the table below.

TABLE 1

X-ray powder diffraction pattern for AHU377 calcium salt, Modification B

| No. | Angle 2θ (°) (±0.1°) | Relative intensity (%) |
|---|---|---|
| 1 | 4.6 | 100 |
| 2 | 6.0 | 78 |
| 3 | 7.1 | 12 |
| 4 | 9.3 | 5 |
| 5 | 11.1 | 9 |
| 6 | 12.0 | 10 |
| 7 | 12.6 | 19 |
| 8 | 14.0 | 12 |
| 9 | 14.4 | 11 |
| 10 | 14.7 | 17 |
| 11 | 15.5 | 18 |
| 12 | 16.6 | 18 |
| 13 | 18.1 | 14 |
| 14 | 19.6 | 26 |
| 15 | 20.7 | 10 |
| 16 | 21.1 | 11 |
| 17 | 21.6 | 12 |
| 18 | 22.5 | 18 |
| 19 | 24.6 | 8 |
| 20 | 25.3 | 8 |
| 21 | 25.5 | 7 |
| 22 | 31.5 | 4 |

The X-ray diffraction changes with hydration level of Modification B. The above x-ray pattern is obtained under ambient conditions, i.e. at a temperature between 20° C. and 25° C., and a relative humidity between 40% and 65%.

The data listed below show the total solvent loss (LOD by thermogravimetry (TG)) and thermal transitions (DTA signals) show the temperature at which the solvent is lost. Modification B shows one endotherm at 173° C. that is indicative of this crystalline form.

TABLE 2

Solvent loss as a function of temperature as measured by TG/DTA

| Form | Loss on drying (LOD) (%) | Thermal transition of LOD (° C.) |
|---|---|---|
| B | No solvent loss up to melt decomposition | 173 (melt decomposition) |

Properties of Modification B

Modification B is highly crystalline and only slightly hygroscopic under typical humidity levels (<2% up to 75% RH). Modification B is highly crystalline and only slightly hygroscopic under typical humidity levels (<2% up to 75% RH). Modification B is thermally stable up to its melting point. Water uptake of Modification B can reach up to 11%. Hydrate formation was observed by wet granulation with water or equilibration in water of ethanol/water 1:1.

Example 3: Synthesis of AHU377 Calcium Salt—Amorphous

A solution of AHU377 sodium salt (4.33 g) in water (40 mL) at 25° C. is treated with a solution of calcium chloride (0.74 g) in water (10 mL). The resulting suspension is further stirred at 25° C. for 2 h, and then filtered. The filter cake is washed with water (10 mL), then dried at 50 C under reduced pressure to provide amorphous AHU377 calcium salt.

When characterized by powder X-ray diffraction, amorphous AHU377 calcium salt gives the pattern shown in FIG. 5. The characteristic peaks (±0.1°) are given in the table below.

The data listed below show the total solvent loss (LOD by thermogravimetry (TG)) and thermal transitions (DTA signals) show the temperature at which the solvent is lost. Amorphous AHU377 calcium salt shows one endotherm at 204° C. that is indicative of this form.

TABLE 3

X-ray powder diffraction pattern for amorphous AHU377 calcium salt

| No. | Angle 2θ (°) (±0.1°) | Relative intensity (%) |
|---|---|---|
| 1 | 3.7 | 100 |

TABLE 4

Solvent loss as a function of temperature as measured by TG/DTA

| Form | Loss on drying (LOD) (%) | Thermal transition of LOD (° C.) |
|---|---|---|
| Amorphous | No solvent loss up to melt decomposition | 204 (melt decomposition) |

Properties of Amorphous AHU377 Calcium Salt

Wet granulation of amorphous AHU377 calcium salt rapidly leads to hydrate formation. When exposed to elevated humidity (>75% RH), amorphous AHU377 calcium salt turns into a crystalline hydrate.

Amorphous AHU377 calcium salt shows a water uptake of 15.2% at 80% RH. No change of the amorphous form was observed by XRPD after compression for 5 min at 10 t or grinding. Wet granulation of amorphous AHU377 calcium salt rapidly leads to hydrate formation. When exposed to elevated humidity (>75% RH), amorphous AHU377 calcium salt turns into a crystalline hydrate.

Example 4: Synthesis of AHU377 Calcium Salt—Modification A

Amorphous AHU377 calcium salt is dissolved in absolute ethanol at 25° C. Upon stirring at 25° C., precipitation of solid AHU377 calcium salt occurs. The solid is filtered and dried under reduced pressure to provide AHU377 calcium salt, Modification A.

When characterized by X-ray powder diffraction, Modification A gives the pattern shown in FIG. 1. The characteristic peaks (±0.1°) are given in the table below.

TABLE 5

X-ray powder diffraction pattern for AHU377 calcium salt, Modification A

| No. | Angle 2θ (°) (±0.1°) | Relative intensity (%) |
|---|---|---|
| 1 | 3.6 | 62 |
| 2 | 5.1 | 100 |
| 3 | 10.7 | 4 |
| 4 | 11.7 | 4 |
| 5 | 12.2 | 3 |
| 6 | 13.1 | 4 |
| 7 | 15.1 | 6 |
| 8 | 15.8 | 9 |
| 9 | 17.3 | 5 |
| 10 | 17.8 | 5 |
| 11 | 20.7 | 8 |
| 12 | 21.7 | 16 |
| 13 | 23.0 | 4 |
| 14 | 25.0 | 4 |
| 15 | 26.8 | 4 |

The X-ray diffraction changes with the hydration level of Modification A. The above X-ray pattern is obtained under ambient conditions, i.e. at a temperature between 20° C. and 25° C., and a relative humidity between 40% and 65%.

The data listed below show the total solvent loss (LOD by thermogravimetry (TG)) and thermal transitions (DTA signals) show the temperature at which the solvent is lost. Modification A shows one endotherm at 192° C. that is indicative of this crystalline form.

TABLE 6

Solvent loss as a function of temperature as measured by TG/DTA

| Form | Loss on drying (LOD) (%) | Thermal transition of LOD (° C.) |
|---|---|---|
| A | No solvent loss up to melt decomposition | 192 (melt decomposition) |

Properties of Modification A

Modification A is hygroscopic.

Modification A shows a water uptake of 13.8% at 95% RH.

Example 5: Synthesis of AHU377 Calcium Salt—Modification C

Amorphous AHU377 calcium salt is dissolved in acetonitrile at 50° C. Upon stirring at 50° C., precipitation of solid AHU377 calcium salt occurs. The solid is filtered and dried under reduced pressure to provide AHU377 calcium salt, Modification C.

When characterized by X-ray powder diffraction, Modification C gives the pattern shown in FIG. 3. The characteristic peaks (±0.1°) are given in the table below.

TABLE 7

X-ray powder diffraction pattern for AHU377 calcium salt, Modification C

| No. | Angle 2θ (°) (±0.1°) | Relative intensity (%) |
|---|---|---|
| 1 | 4.6 | 100 |
| 2 | 6.2 | 34 |
| 3 | 14.5 | 29 |
| 4 | 15.4 | 41 |
| 5 | 20.4 | 53 |
| 6 | 21.7 | 21 |
| 7 | 22.1 | 18 |

The X-ray diffraction changes with hydration level with Modification C. The above X-ray pattern is obtained under ambient conditions, i.e. at a temperature between 20° C. and 25° C., and a relative humidity between 40% and 65%.

The data listed below show the total solvent loss (LOD by thermogravimetry (TG)) and thermal transitions (DTA signals) show the temperature at which the solvent is lost. Modification C shows one endotherm at 180.0° C. that is indicative of this crystalline form.

TABLE 8

Solvent loss as a function of temperature as measured by TG/DTA

| Form | Loss on drying (LOD) (%) | Thermal transition of LOD (° C.) |
|---|---|---|
| C | No solvent loss up to melt decomposition | 180.0 (melt decomposition) |

Example 6: Synthesis of AHU377 Calcium Salt—Modification $H_B$, Procedure 1

A solution of AHU377 sodium salt (20.37 g) in water (120 mL), with the sodium salt prepared according to the procedure given in Example 8, is concentrated at 50° C. under reduced pressure to remove all residual isopropyl acetate. After concentration, the solution is diluted with water to the original volume. The solution of AHU377 sodium salt in water is heated to 83° C. over 30 min, then a solution of calcium chloride (2.61 g) in water (104 mL) is added over 1 h. The resulting suspension is stirred at 83° C. for 4.5 h. The temperature is decreased to 65° C. over 90 min, and then increased again to 83° C. over 30 min. This cycle is repeated another three times. The reaction mixture is then cooled to 50° C. over 2 h and further stirred at this temperature for 2 h. The crystals are collected by filtration at 50° C., and the filter cake is washed with water (2×65 mL) at 50° C. The solids are dried at 60° C. under reduced pressure to give AHU377 calcium salt, Modification $H_B$.

Figure 4:
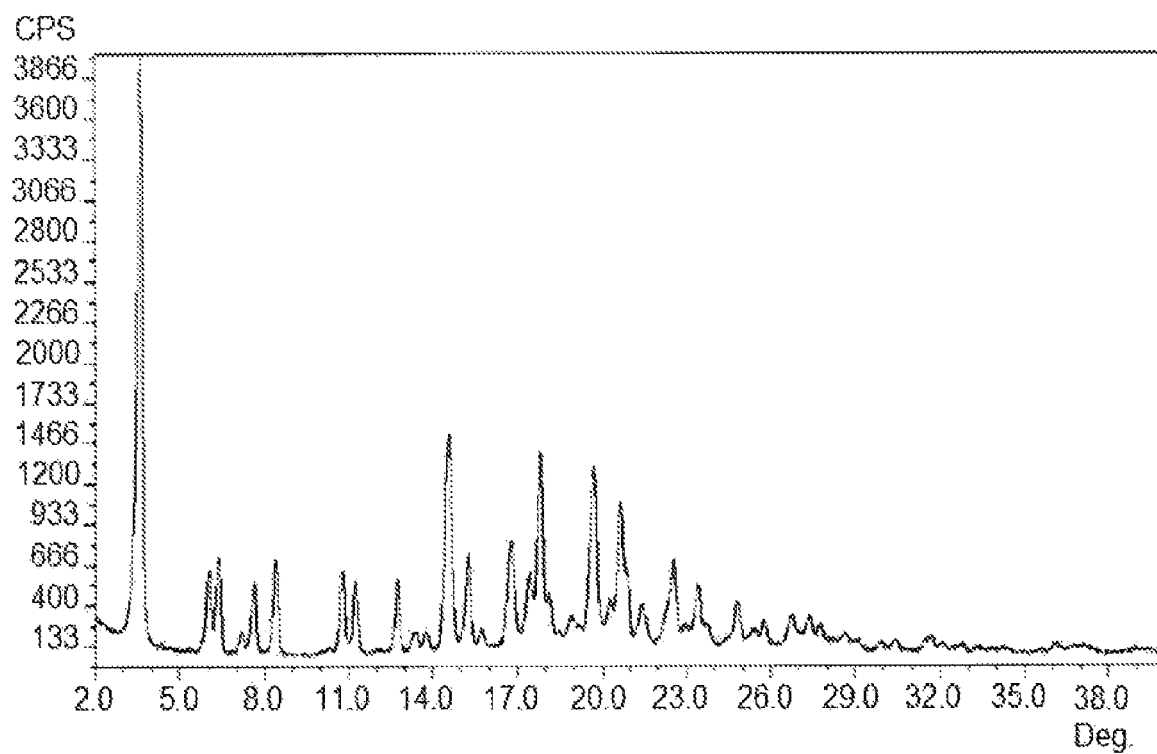
FIG. 4 illustrates the x-ray powder diffraction (XRPD) pattern of Modification $H_B$.

When characterized by X-ray powder diffraction, Modification $H_B$ gives the pattern shown in FIG. 4. The characteristic peaks (±0.1°) are given in the table below.

TABLE 9

X-ray diffraction pattern for AHU377 calcium salt, Modification $H_B$

| No. | Angle 2θ (°) (±0.1°) | Relative intensity (%) |
|---|---|---|
| 1 | 3.6 | 100 |
| 2 | 6.1 | 15 |
| 3 | 6.4 | 18 |
| 4 | 7.6 | 13 |
| 5 | 8.4 | 17 |
| 6 | 10.8 | 15 |
| 7 | 11.3 | 14 |
| 8 | 12.8 | 14 |
| 9 | 14.6 | 37 |
| 10 | 15.3 | 18 |
| 11 | 16.8 | 20 |
| 12 | 17.8 | 35 |
| 13 | 19.7 | 32 |
| 14 | 20.6 | 27 |
| 15 | 21.4 | 10 |
| 16 | 22.5 | 17 |
| 17 | 23.4 | 13 |
| 18 | 24.8 | 11 |

The X-ray diffraction changes with the hydration level of Modification $H_B$. The above X-ray pattern is obtained under ambient conditions, i.e. at a temperature between 20° C. and 25° C., and a relative humidity between 40% and 65%.

Modification $H_B$ is particularly suitable for industrial scale-up. It is a crystalline form which remains dry at 25° C. and at relative humidity ranging from 0% to 80%.

The data listed below show the total solvent loss (LOD by thermogravimetry (TG)) and thermal transitions (DTA signals) show the temperature at which the solvent is lost. Modification $H_B$ shows three endotherms at 98° C., 134° C. and 180° C. that are indicative of this crystalline form.

TABLE 10

Solvent loss as a function of temperature as measured by TG/DTA

| Form | Loss on drying (LOD) (%) | Thermal transition of LOD (° C.) |
|---|---|---|
| $H_B$ | 3.4 | 98, 134, 180 |

Properties of Modification $H_B$

Modification $H_B$ is obtained with water levels in the range 1.4-4.1%. Complete dehydration requires heating above 97° C., and the melt decomposition begins above 180° C. Modification $H_B$ shows good flowability properties.

The water uptake of modification $H_B$ at 95% RH is 2.0%. Modification $H_B$ is retained during take-up and release of water (e.g. in sorption-desorption experiments).

Example 7: Synthesis of AHU377 Calcium Salt—Modification HB, Procedure 2

To a solution of AHU377 sodium salt (20.37 g) in water (120 mL), said sodium salt prepared according to the procedure given in Example 8, is heated to 50° C., then isopropyl acetate (12.9 mL) is added. A solution of calcium chloride (2.61 g) in water (104 mL) is added over 1 h. The resulting suspension is stirred at 50° C. for 15 h. The solids are isolated by filtration, then charged back into the reaction flask, suspended in water (240 mL) and isopropyl acetate (8 mL), and stirred at 50° C. for 20 min. The solids are isolated by filtration, then charged back into the reaction flask, suspended in water (240 mL), and stirred at 50° C. for 20 min. Filtration and drying at 60° C. under reduced pressure gives AHU377 calcium salt, Modification $H_B$.

Example 8: AHU377 Sodium Salt

The sodium salt of AHU377 used e.g. in Example 3 is synthesized from AHU377 free acid by treatment with sodium hydroxide, according to the generic scheme below.

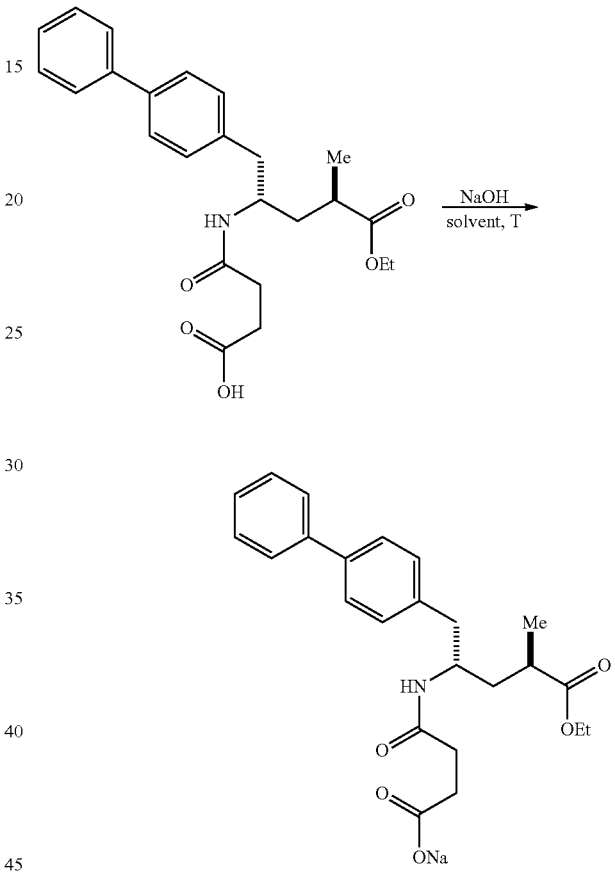

In most cases, the solution of AHU377 in isopropyl acetate, prepared according to the process described in Example 1, is used. The sodium salt of AHU377 is generally not isolated as the pure substance, but is used as solution in water after treatment of the solution of AHU377 in isopropyl acetate with aqueous sodium hydroxide:

To a solution of the free acid of AHU377 (88.7 g, 1.00 equiv.) in isopropyl acetate (850 ml) at room temperature is added a solution of sodium hydroxide (8.62 g, 1.00 equiv.) in water (270 ml). The biphasic mixture is heated to 50° C., and then stirred at this temperature for 15 min. After phase separation at 50° C., the organic layer is extracted with water (105 ml). The combined aqueous phases are washed with isopropyl acetate (2×255 ml) to give a solution of the sodium salt of AHU377 in water, which is directly used without further purification.

In the present examples, the free acid of AHU377 was prepared as follows by acylation of the amine (according to the scheme shown in WO 2008/031567):

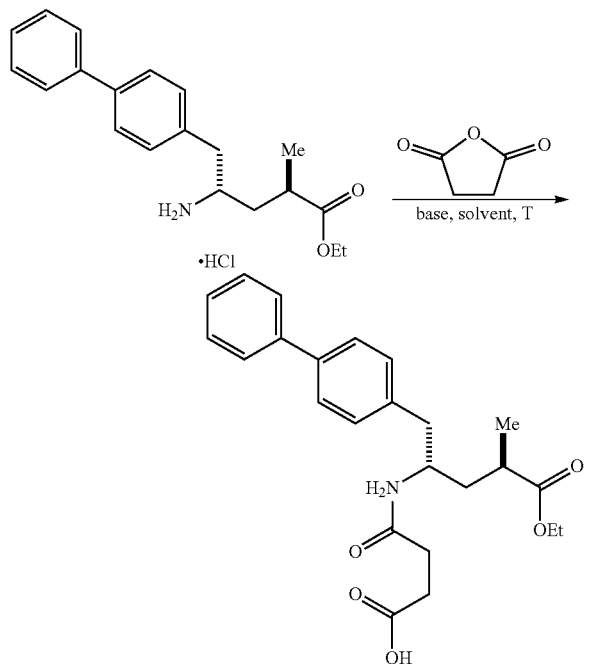

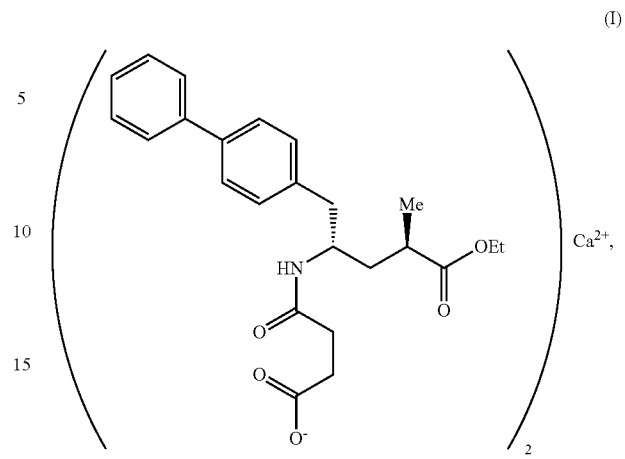

To a suspension of ethyl (2R,4S)-5-([1,1'-biphenyl]-4-yl)-4-amino-2-methylpentanoate hydrochloride (100 g, 1.00 equiv.), prepared as described in U.S. Pat. No. 5,217,996, and succinic anhydride (33.1 g, 1.15 equiv.) in isopropyl acetate (800 ml) at 0° C., a solution of triethylamine (51 ml, 1.28 equiv.) in isopropyl acetate (100 ml) is added over 1 h. The reaction mixture is further stirred at 0° C. for 1 h, then warmed to room temperature over 1 h. The reaction is quenched by addition of a solution of citric acid (68.5 g, 1.24 equiv.) in water (300 ml). After phase separation, the organic layer is washed with water (2×200 ml) to give a solution of the free acid of AHU277 in isopropyl acetate, which is directly used without further purification in the next step (see Example 8). The free acid of AHU377 can be obtained as pure substance by concentration of the solution in isopropyl acetate for use without further purification in the next step (see Example 1).

Example 9: Capsule

The following is an example of a pharmaceutical dosage form suitable for use in the present invention:

Preparation of 1,000 capsules each containing as active ingredient 50 mg of AHU377 calcium salt Modification B 50.00 g of active ingredient, 187.00 g of lactose, 80.00 g of modified starch and 3.00 g of magnesium stearate are each passed through a screen with openings of 0.6 mm. The drug substance is placed in a suitable mixer and mixed first with magnesium stearate, then with lactose and starch until homogenous. No. 2 hard gelatin capsules are filled with 300 mg of said mixture each, using a capsule filling machine.

The invention claimed is:

1. A crystalline form of a calcium salt of N-(3-carboxyl-1-oxopropyl)-(4S)-(p-phenylphenylmethyl) -4-amino-(2R)-methyl butanoic acid ethyl ester having the formula (I)

wherein the crystalline form is Modification B or hydrate form $H_B$, wherein

Modification B is characterized in that said form has an X-ray powder diffraction pattern comprising 2θ values (±0.1°) (CuKα; 45 kV, 40 mA;λ=1.540598 Å) selected from 4.6, 6.0, 12.6, 15.5, 16.6, 19.6 and 22.5 degrees at a temperature of 20 to 25° C., and Modification $H_B$ is characterized in that said form has an X-ray powder diffraction pattern comprising 2θ values (±0.1°) (CuKα; 45 kV, 40 mA;λ=1.540598 Å) selected from 3.6, 6.4, 8.4, 14.6, 15.3, 16.8, 17.8, 19.7 and 20.6 degrees at a temperature of 20 to 25° C.

2. The crystalline form according to claim 1, wherein the crystalline form is Modification B, and wherein Modification B is characterized by a powder x-ray diffraction pattern further comprising 2θ values (±0.1°) (CuKa; 45 kV, 40 mA;λ=1.540598 Å) selected from 7.1, 9.3, 11.1, 12.0, 14.0, 14.4, 14.7, 18.1, 20.7, 21.1, 21.6, 24.6, 25.3, 25.5, and 31.5 at a temperature of 20 to 25° C.

3. A pharmaceutical composition comprising a crystalline form according to claim 1, and one or more pharmaceutically acceptable carrier or excipient.

4. The pharmaceutical composition according to claim 3, wherein said crystalline form is selected from the group consisting of Modification B, Modification $H_B$ and combinations thereof.

5. The pharmaceutical composition according to claim 3, in combination with an angiotensin receptor blocker (ARB).

6. The pharmaceutical composition according to claim 4, wherein said crystalline form is Modification B.

7. The pharmaceutical composition according to claim 4, wherein said crystalline form is in substantially pure form.

8. The pharmaceutical composition according to claim 5, wherein the ARB is selected from the group consisting of losartan, irbesartan, candesartan, eprosartan, telmisartan, olmesartan and valsartan, or a pharmaceutically acceptable salt thereof.

9. The pharmaceutical composition according to claim 5, wherein the ARB is valsartan, or a pharmaceutically acceptable salt thereof.

10. The crystalline form according to claim 1, wherein the crystalline form is Modification $H_B$, and wherein Modification $H_B$ is characterized by an X-ray powder diffraction pattern comprising 2θ values (±0.1°) (CuKa; 45 kV, 40 mA;λ=1.540598 Å) selected from 3.6, 6.4, 8.4, 14.6, 15.3, 16.8, 17.8, 19.7 and 20.6 degrees at a temperature of 20 to 25° C.

11. The crystalline form according to claim 1, wherein the crystalline form is Modification B, and wherein Modification B has at least one, two, three, or all of the following characteristics:
   i) an X-ray powder diffraction pattern substantially in accordance with the X-ray powder diffraction spectrum shown in FIG. 2;
   ii) a melting point with an onset at 173±2.4° C.;
   iii) a differential thermal analysis (DTA) thermogram with an endotherm starting at 173±2.5° C.;
   iv) a differential thermal analysis (DTA) thermogram substantially the same as that shown in FIG. 7; and
   v) a thermogravimetric analysis (TGA) diagram substantially the same as that shown in shown in FIG. 7.

Figure 9:
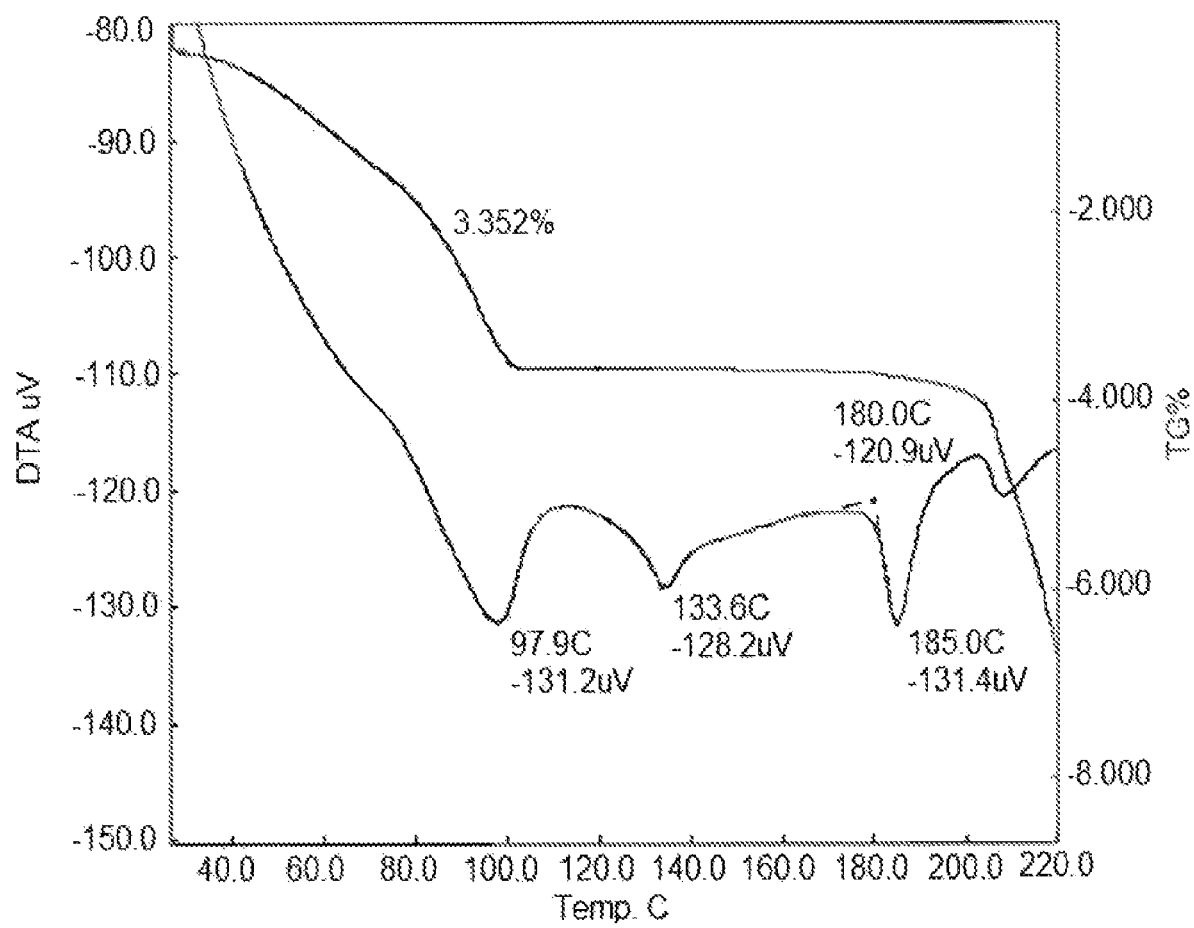
FIG. 9 illustrates the thermogravimetric analysis (TGA) of the Modification $H_B$.
Figure 10:
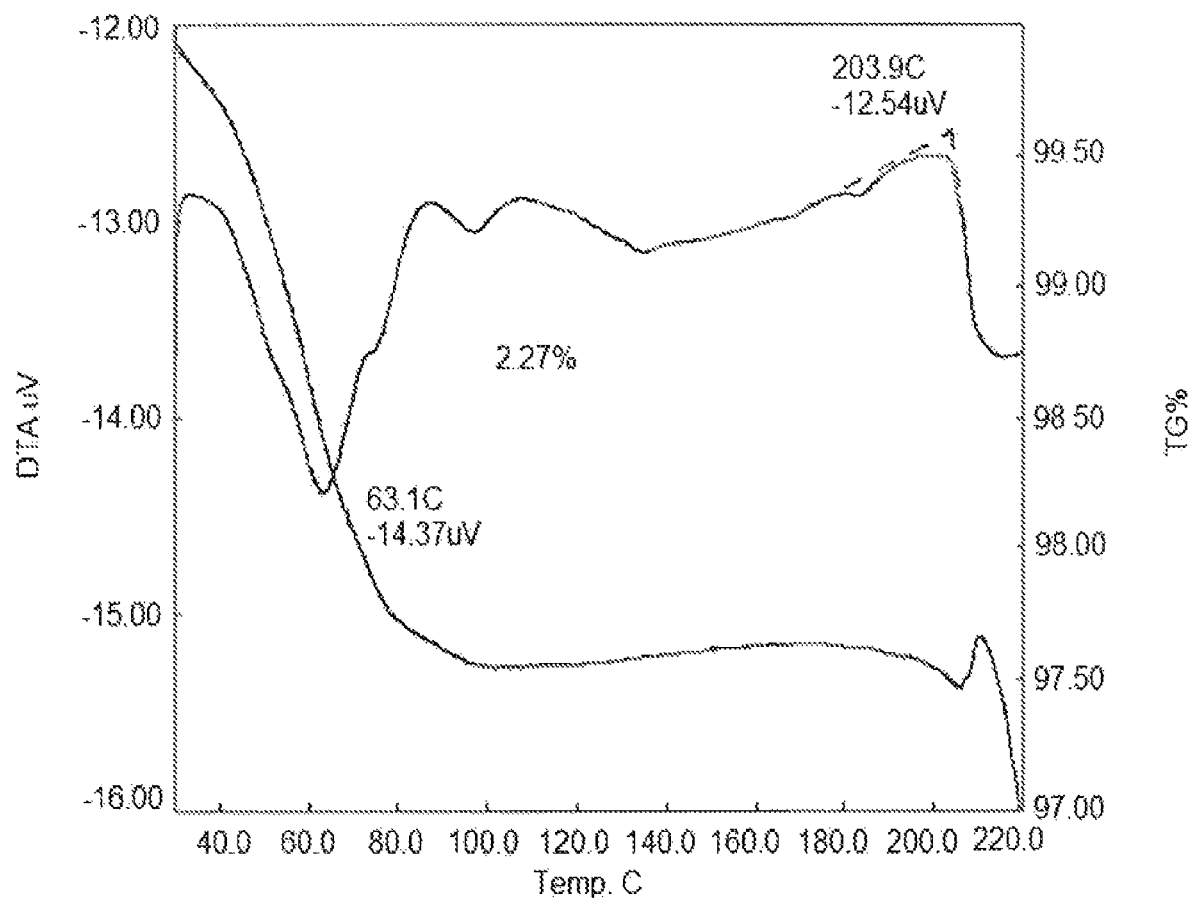
FIG. 10 illustrates the thermogravimetric analysis (TGA) of the amorphous calcium salt of AHU377.

12. The crystalline form according to claim 1, wherein the crystalline form is Modification $H_B$, and wherein Modification $H_B$ has at least one, two, three, or all of the following characteristics:
   i) an X-ray powder diffraction pattern substantially in accordance with the X-ray powder diffraction spectrum shown in FIG. 4;
   ii) a melting point with an onset at 180±2.4° C.;
   iii) a differential thermal analysis (DTA) thermogram with an endotherm starting at 180±2.5° C.; and
   iv) a differential thermal analysis (DTA)/TGA thermogram substantially the same as that shown in shown in FIG. 9.

\* \* \* \* \*